United States Patent
Brown et al.

(10) Patent No.: US 6,600,028 B1
(45) Date of Patent: Jul. 29, 2003

(54) TRICYCLIC BASE ANALOGUES

(75) Inventors: Daniel Brown, Cambridge (GB); David Loakes, Letchworth (GB); David Williams, Sheffield (GB); Fergal Hill, Cambridge (GB); Shiv Kumar, Belle Mead, OH (US); Satyam Nampalli, Belle Mead, OH (US); Mark McDougall, Bethlehem, PA (US); Alan Hamilton, Amersham (GB); Clifford Smith, Tring (GB); Adrian Christopher Simmonds, Amersham (GB); William Jonathan Cummins, Tring (GB); Patrick Finn, Belle Mead, NJ (US)

(73) Assignee: Amersham Pharmacia Biotech UK Limited, Buckinghamshire (GB)

( * ) Notice: Subject to any disclaimer, the term of this patent is extended or adjusted under 35 U.S.C. 154(b) by 0 days.

(21) Appl. No.: 09/402,048

(22) PCT Filed: Apr. 2, 1998

(86) PCT No.: PCT/GB98/00978
§ 371 (c)(1),
(2), (4) Date: Feb. 1, 2000

(87) PCT Pub. No.: WO98/43991
PCT Pub. Date: Oct. 8, 1998

(30) Foreign Application Priority Data

Apr. 2, 1997 (EP) .............................. 97302265

(51) Int. Cl.$^7$ .......................... C07H 21/00; G01N 33/53
(52) U.S. Cl. .................. 536/23.1; 536/24.3; 536/26.23; 536/26.26; 536/26.6; 536/27.1; 435/7.2; 435/91.2
(58) Field of Search ............. 536/23.1, 24.3, 536/26.23, 26.26, 26.6, 27.1; 435/7.2, 91.2

(56) References Cited

U.S. PATENT DOCUMENTS

| | | | | |
|---|---|---|---|---|
| 4,123,524 A | * | 10/1978 | Townsend et al. | 514/43 |
| 5,633,235 A | * | 5/1997 | Townsend et al. | 514/49 |
| 6,153,745 A | * | 11/2000 | Williams et al. | 536/25.32 |
| 6,239,159 B1 | * | 5/2001 | Brown et al. | 514/394 |
| 6,313,286 B1 | * | 11/2001 | Brown et al. | 536/27.1 |

FOREIGN PATENT DOCUMENTS

| | | | |
|---|---|---|---|
| WO | WO 95/06752 | | 9/1995 |
| WO | WO 98/43991 A1 | * | 10/1998 |
| WO | WO 99/06422 A2 | * | 2/1999 |

OTHER PUBLICATIONS

Bennett et al., "Biochemical Properties of the Nucleoside of 3–Amino–1, 5–dihydro–5–methyl–1,4,5,6,8–pentaazaacenaphthylene (NSC–154020)," *Biochemical Pharmacology*, 27(2), 233–241 (1978).*

Wotring et al.(I), "Effects of the Tricyclic Nucleoside 6–Amino–4–methyl–8–(β–D–ribofuranosyl)–pyrrolo[4,3, 2–de]pyrimido[4,5–c]pyridazine on the Viability and Cell Cycle Distribution of L1210 Cells in Vitro," *Cancer Research*, 45, 6355–6361 (Dec., 1985).*

Wotring et al.(II), "Dual Mechanisms of Inhibition of DNA Synthesis by Triciribine," *Cancer Research*, 50, 4891–4899 (Aug. 15, 1990).*

Williams et al., "The Synthesis of a Tricyclic Pyrrolopyrimidine Related to N$^6$–hydroxyadenine," *Journal of the Chemical Society, Perkin Transaction I*, (Issue No. 8), 1171–1178 (Apr. 21, 1997).*

Abdelhamid, "Heterocyclic Synthesis Using Hydrazonoyl Halides: Synthesis of Annulated Pyrimidines, Pyridazines and Pyrazoles," *Journal of Chemical Research, Synop.*, 1993(6), 208–209; *Chemical Abstracts*, 120(11), p. 1033, Abstract No. 134404q (Mar. 14, 1994); only abstract supplied.*

Kawasaki et al., "Synthesis and Cytotoxicity Studies of 8–Amino–6–methyl–2–β–D–ribofuranosyl–1,2,3,5,6, 7–hexaazaacenaphthylene (7–Aza–TCN) and the Corresponding 2'–Deoxy–and Arabinonucleoside Analogues," *Journal of Medicinal Chemistry*, 33(12), 3170–3176 (Dec., 1990).*

Van Sickle et al., "The Synthesis of 8–Amino–6–N–methyl–1,2,3,5,6,7–hexaazaacenaphthylene," *Heterocycles*, 30(2), 963–969 (Apr. 1, 1990).*

(List continued on next page.)

*Primary Examiner*—James O. Wilson
*Assistant Examiner*—Lawrence Crane
(74) *Attorney, Agent, or Firm*—Marshall, Gerstein & Borun

(57) ABSTRACT

Nucleoside analogues have structure (2) wherein Q is H or a sugar moiety or sugar analogue or a modified sugar or a nucleic backbone or backbone analogue, W is an alkylene or alkenylene chain of 0–5 carbon atoms, any of which may carry a substituent $R^8$, X is O or N or $NR^{12}$ or $CR^{10}$, X' is O or S or N, provided that when X' is O or S, then X is C, Y is CH or N, $R^6$ is $NH_2$ or SMe or $SO_2Me$ or $NHNH_2$, each of $R^7$ and $R^8$ is independently H or F or alkyl or alkenyl or aryl or acyl or a reporter moiety, $R^{12}$ is independently H or alkyl or alkenyl or aryl or acyl or a reporter moiety, and $R^{10}$ is H or =O or F or alkyl or aryl or a reporter moiety.

(2)

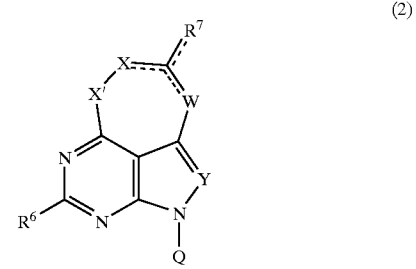

14 Claims, No Drawings

OTHER PUBLICATIONS

Townsend et al.(III), "The Synthesis and Biological Activity of Certain Pentaazaacenaphthylenes, Hexaazaacenaphthylenes and Their Corresponding Nucleosides," Fourteenth Symposium on Nucleic Acids Chemistry, M. Honjo (ed.), Tokushima, Japan, Oct. 30–Nov. 1, 1986, also published in *Nucleic Acids Symposium Series, No. 17*, IRL Press Ltd., Oxford, England, 1986, see pp. 41–44.*

Tomasz et al., "5'–P–Borane—Substituted Thymidine Monophosphate and Triphosphate," *Angewandte Chemie, International Edition, 31*(10), 1373–1375 (1992).*

Williams et al, (III), "Some Pyrrolopyrimidine Chemistry Directed to the Synthesis of Tricyclic Purine Analogues," *Journal of the Chemical Society, Perkin Transaction 1*, (Issue No. 10), 1225–1231 (May 21, 1995).*

* cited by examiner

TRICYCLIC BASE ANALOGUES

This applicant is a 371 of PCT/GB98/00978, filed Apr. 2, 1998, and claims priority from EPO Application No. 97302265.0, filed Apr. 2, 1997.

This invention concerns base analogues which may be used to make nucleoside analogues and nucleotide analogues which may be incorporated into nucleic acids. Some of these analogues are base-specific and may be incorporated into DNA or RNA in the place of a single native base i.e. A, T, G, or C. Other analogues have the potential for base-pairing with more than one native base or base analogue.

The 2'-deoxyribosides of such analogues as (1) (P: Kong Thoo Lin and Brown, 1989, Nucleic Acids Research, 17, 10373–83), N6-methoxyadenine and N6-methoxy-2,6-diaminopurine have been shown to be extremely useful in mixed sequence oligonucleotide primers used in PCR and DNA sequencing. In addition, the base pairing characteristics of the 2'-deoxynucleoside 5'-triphosphate of P have been exploited in a PCR-based random mutagenesis procedure (Zaccolo et al, 1996, J. Mol. Biol., 255, 589–603):

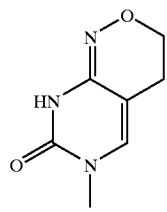
(1)

Synthesis of a nucleoside with a tricyclic base analogue where the third ring is between the 6 and 7 positions (purine nomenclature) was described by Schram and Townsend (1971) Tetrahedron Lett 49,. 4757–4760. However, this has a blocked hydrogen bonding face and would not be expected to participate in base pairing observed in native nucleic acids or, as a triphosphate, in polymerase mediated incorporation reactions.

The present invention provides a compound having the structure(2)

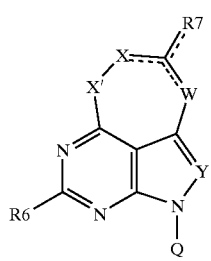
(2)

where

W is an alkylene or alkenylene chain of 0–5 carbon atoms any of which may carry a substituent $R^8$, X is O or N or $NR^{12}$ or $CR^{10}$, X' is O or S or N, provided that when X' is O or S, X is C, Y is CH or N, $R^6$ is H or $NH_2$ or SMe or $SO_2Me$ or $NHNH_2$, each of $R^7$ and $R^8$ is independently H or F or alkyl or alkenyl or aryl or acyl or a reporter moiety, each of $R^9$ and $R^{12}$ is independently H or alkyl or alkenyl or aryl or acyl or a reporter moiety, $R^{10}$ is H or =O or F or alkyl or alkenyl or aryl or acyl or a reporter moiety, the dotted line indicates one optional double bond, Q is H or a sugar moiety or a sugar analogue including but not limited to the structure

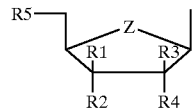

where

Z is O, S, Se, SO, $NR^9$ or $CH_2$, $R^1$, $R^2$, $R^3$ and $R^4$ are the same or different and each is H, OH, F, $NH_2$, $N_3$, O-hydrocarbyl or a reporter moiety, $R^5$ is OH, SH or $NH_2$ or mono-, di- or tri-phosphate or -thiophosphate, or corresponding boranophosphate, or one of $R^2$ and $R^5$ is a phosphoramidite or other group for incorporation in a polynucleotide chain, or a reporter moiety, or Q consists of one of the following modified sugar structures Acyclic Sugars

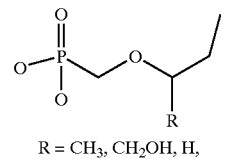

R = $CH_3$, $CH_2OH$, H,

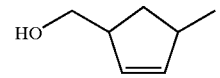

Morpholino Backbone

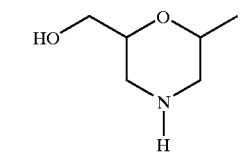

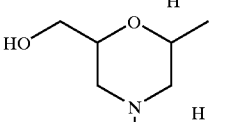

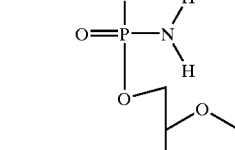

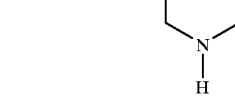

or Q is a nucleic acid backbone consisting of sugar-phosphate repeats or modified sugar-phosphate repeats (e.g. LNA) (Koshkin et al, (1998), Tetrahedron 54, 3607–30), or a backbone analogue such as peptide or polyamide nucleic acid (PNA). (Nielsen et al, 1991, Science 254, 1497–1500).

Preferably:

W=CH$_2$
X=O
X'=N
Y=CH or N
R$^6$=H or NH$_2$
R$^7$=H or reporter moiety.

The dotted line in the structure (2) shows that either —X—CHR$^7$—W— or —X=CR$^7$—W— or —X—CR$^7$=W— is present. Of course, when X is O the second of these structures is not possible.

Depending on the identity of W, the ring containing X' and X contains from 6 to 11 members.

Alkyl, alkenyl, aryl and acyl groups herein preferably contain 1–20 carbon atoms.

Any unfilled valencies are to be understood as being filled by H.

The 2-deoxynucleoside analogue termed as P (Kong, Thoo Lin and Brown, 1989, Nucleic Acids Research 17, 10373–83) can exist in two tautomeric forms as indicated below:

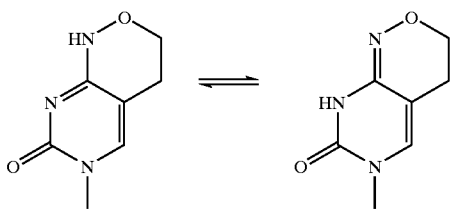

Base analogues of this invention where X'=N and X=O or N or CR$^{10}$ also exhibit similar types of tautomerism, e.g.

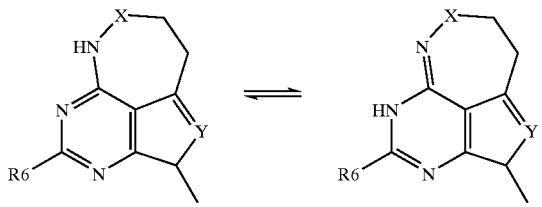

The exact ratio of these tautomers can be affected by the X substituent. The changes in tautomeric ratio can have subtle effects on the hybridisation properties of the analogue. For convention only one tautomer is drawn within this patent though it is implicit that both can be present.

When Q is H, these compounds are base analogues. When Q is a sugar moiety or sugar analogue or a modified sugar, these compounds are nucleotide analogues or nucleoside analogues. When Q is a nucleic acid backbone or a backbone analogue, these compounds are herein called nucleic acids or polynucleotides.

In the context of the this invention, a nucleotide is a naturally occurring compound comprising a base and a sugar backbone including a phosphate. A nucleoside is a corresponding compound in which a backbone phosphate may or may not be present. Nucleotide analogues and nucleoside analogues are analogous compounds having different bases and/or different backbones. A nucleoside analogue is a compound which is capable of forming part of a nucleic acid (DNA or RNA) chain, and is there capable of base-pairing with a base in a complementary chain or base stacking in the appropriate nucleic acid chain. A nucleoside analogue may be specific, by pairing with only one complementary nucleotide; or degenerate, by base pairing with two or three of the natural bases, e.g. with pyrimidines (T/C) or purines (A/G); or universal, by pairing with each of the natural bases without discrimination; or it may pair with another analogue or itself.

In one preferred aspect of the invention, the base analogue is linked to a sugar moiety such as ribose or deoxyribose to form a nucleoside analogue. When the group R$^5$ is triphosphate, the nucleoside triphosphate analogues of the invention are capable of being incorporated by enzymatic means into nucleic acid chains.

In another preferred aspect, the nucleoside analogue or nucleotide analogue which contains a base analogue as defined is labelled with at least one reporter moiety. A reporter moiety may be any one of various things. It may be a radioisotope by means of which the nucleoside analogue is rendered easily detectable, for example 32-P or 33-P or 35-S incorporated in a phosphate or thiophosphate or phosphoramidite or H-phosphonate group, or alternatively 3-H or 14-C or an Iodine isotope. It may be an isotope detectable by mass spectrometry or NMR. It may be a signal moiety e.g. an enzyme, hapten, fluorophore, chromophore, chemiluminescent group, Raman label, electrochemical label or signal compound adapted for detection by mass spectrometry. The reporter moiety may comprise a signal moiety and a linker group joining it to the remainder of the molecule, which linker group may be a chain of up to 30 carbon, nitrogen, oxygen and sulphur atoms, rigid or flexible, unsaturated or saturated as well known in the field. The reporter moiety may comprise a solid surface and a linker group joining it to the rest of the molecule. Linkage to a solid surface enables the use of nucleic acid fragments containing nucleoside analogues to be used in assays including bead based probe assays or assays involving arrays of nucleic acid samples or oligonucleotides which are interrogated with e.g. oligonucleotide or nucleic acid probes. The reporter moiety may consist of a linker group with a terminal or other reactive group, e.g. NH$_2$, OH, COOH, CONH$_2$ or SH, by which a signal moiety and/or solid surface may be attached, before or after incorporation of the nucleoside analogue in a nucleic acid chain, before or after hybridisation.

Two (or more) reporter groups may be present, e.g. a signal group and a solid surface, or a hapten and a different signal group, or two fluorescent signal groups to act as donor and acceptor. Various formats of these arrangements may be useful for separation purposes.

Purine and pyrimidine nucleoside derivatives labelled with reporter moieties are well known and well described in the literature. Labelled nucleoside derivatives have the advantage of being readily detectable during sequencing or other molecular biology techniques.

R$^1$, R$^2$, R$^3$ and R$^4$ may each be H, OH, F, NH$_2$, N$_3$, O-alkyl or a reporter moiety. Thus ribonucleosides, and deoxyribonucleosides and dideoxyribonucleosides are envisaged together with other nucleoside analogues. These sugar substituents may contain a reporter moiety in addition to one or two present in the base.

R$^5$ is OH, SH, NH$_2$ or mono-, di- or tri-phosphate or -thiophosphate or corresponding boranophosphate. Alternatively, one of R$^2$ and R$^5$ may be a phosphoramidite or H-phosphonate or methylphosphonate or phosphorothioate, or an appropriate linkage to a solid surface e.g. hemisuccinate controlled pore glass, or other group for incorporation, generally by chemical means, in a polynucleotide chain. The use of phosphoramidites and related derivatives in synthesising oligonucleotides is well known and described in the literature.

In the new base or nucleoside analogues to which this invention is directed, at least one reporter moiety is preferably present in the base analogue or in the sugar moiety or a phosphate group. Reporter moieties may be introduced into the sugar moiety of a nucleoside analogue by literature methods (e.g. J. Chem. Soc. Chem. Commun. 1990, 1547–8; J. Med. Chem., 1988, 31. 2040–8). Reporters in the form of isotopic labels may be introduced into phosphate groups by literature methods (Analytical Biochemistry, 214, 338–340, 1993; WO 95/15395).

Examples within this specification have shown how analogues where W is one carbon atom can readily be synthesised and how reactive groups and signal moieties can be included as required. It has been found that two basic approaches to tricyclic formation can be undertaken. A leaving group can be generated at the 6 position (purine nomenclature) of the precursor bicyclic base heterocycle and subsequently displaced by an incoming nucleophile species attached to a side arm such as an hydroxylamine derivative in example 1.10. This approach was found to be not applicable under the conditions tried when W=1 and Y=N. Instead, the synthetic approach of initially displacing a leaving group in the 6 position (purine nomenclature) with hydroxylamine (Example 4.8) and then effecting ring closure by reaction of this with triisopropylbenzenesulphonyl chloride and displacement with an alkoxide derivative was found to be effective (Example 4.11). A similar strategy was applied in making 5-β-D-ribofuranosyl-3H,5H,7H-pyrimido[4,5-c][1,2]oxazol-6-one, a bicyclic base analogue (Loakes and Brown, 1994, Nucleosides and Nucleotides 13, 679–706). By such a strategy the previously unmade compound W=zero carbons Y=CH or N could then be prepared.

Nucleoside analogues of this invention are useful for labelling DNA or RNA or for incorporating in oligonucleotides. Some have the possible advantage over conventional hapten labelled nucleotides such as fluorescein-dUTP of being able to replace more than one base. A reporter moiety is attached at a position where it does not have a significant a detrimental effect on the physical or biochemical properties of the nucleoside analogue, in particular its ability to be incorporated in single stranded or double stranded nucleic acid.

A template containing the incorporated nucleoside analogue of this invention may be suitable for copying in nucleic acid synthesis. If a reporter moiety of the incorporated nucleoside analogue consists of a linker group, then a signal moiety can be introduced into the incorporated nucleoside analogue by being attached through a terminal or other reactive group of the linker group.

A nucleoside analogue triphosphate of this invention may be incorporated by enzymes such as terminal transferase to extend the 3' end of nucleic acid chains in a non-template directed manner. Tails of the nucleoside analogue triphosphate produced in this way may be detected directly in the absence of any reporter label by use of antibodies directed against the nucleoside analogue (as described in Example 13 of WO 97/28177). The analogues when incorporated into oligonucleotides or nucleic acids may be acted upon by nucleic acid modification enzymes such as ligases or restriction endonucleases.

In primer walking sequencing, a primer/template complex is extended with a polymerase and chain terminated to generate a nested set of fragments where the sequence is read after electrophoresis and detection (radioactive or fluorescent). A second primer is then synthesised using the sequence information near to the end of the sequence obtained from the first primer. This second ("walking") primer is then used for sequencing the same template. Primer walking sequencing is more efficient in terms of generating less redundant sequence information than the alternative "shot gun" approach.

The main disadvantage with primer walking is the need to synthesise a primer after each round of sequencing. Cycle sequencing requires primers that have annealing temperatures near to the optimal temperature for the polymerase used for the cycle sequencing. Primers between 18 and 24 residues long are generally used for cycle sequencing. The size of a presynthesised walking primer set required has made primer walking cycle sequencing an impractical proposition. The use of base analogues that are degenerate or universal addresses this problem. The use of such analogues that are also labelled, e.g. the nucleoside analogues of this invention will also help to overcome the problem. Preferred reporters for this purpose are radioactive isotopes or fluorescent groups, such as are used in conventional cycle sequencing reactions. Where the nucleoside analogues are base specific chain terminators they may be used in chain terminating sequencing protocols.

The final analysis step in DNA sequencing involves the use of a denaturing polyacrylamide electrophoresis gel to separate the DNA molecules by size. Electrophoretic separation based solely on size requires the complete elimination of secondary structure from the DNA. For most DNA this is typically accomplished by using high concentrations of urea in the polyacrylamide matrix and running the gels at elevated temperatures. However certain sequences, for example those capable of forming "stem loop" structures retain secondary structure and, as a result, display compression artefacts under standard electrophoresis conditions. Here, adjacent bands of the sequence run at nearly the same position on the gel, "compressed" tightly together. Such loops are typically formed when a number of GC pairs are able to interact since GC pairs can form 3 hydrogen bonds compared to the 2 hydrogen bonds of AT pairs.

A second form of compression artefact is seen when rhodamine-labelled terminators are used and there is a G residue close to the terminus. In these cases, anomalous mobility of the DNA strand in a gel is often seen, possibly due to an interaction between the dye and the G residue.

Thus, compression artefacts appear to be caused whenever stable secondary structures exist in the DNA under the conditions prevailing in the gel matrix during electrophoresis. The folded structure runs faster through the gel matrix than an equivalent unfolded DNA.

Currently, gel compression artefacts are eliminated in one of two ways. One is to change to a stronger denaturing condition for the gel, for example 40% formamide with 7 M urea. The other method is to incorporate a derivative of dGTP during the synthesis of DNA.

Two nucleotides are currently used to remove compression artefacts. The first, 7-deazadGTP, can remove specific artefacts seen in fluorescent sequencing where the rhodamine dye-labelled terminator appears to interact with a nearby G residue. It can also reduce Hoogsteen interactions which may contribute to some compression artefacts. However, it does not remove all sequencing artefacts as it still has the same Watson and Crick (and wobble) H bonding capabilities as dGTP. The second nucleotide dITP will remove all sequencing artefacts. It has reduced hydrogen bonding capabilities, so preventing secondary structure being a problem. The downside of this analogue is that it is a very poor DNA polymerase substrate. It requires lower temperature and longer extension times than dGTP in cycle sequencing reactions. This analogue produces sequences with large variations in peak heights (fluorescent sequencing) and band intensities (radioactive sequencing).

In fact it is only really suited to use with [α³³P] ddNTP and ThermoSequenase™ sequencing protocols due to the exceptionally high quality of the banding pattern. Therefore there is a need for a dGTP analogue that is a good DNA polymerase substrate which has the combined characteristics of 7 deaza dGTP and dITP. This may be achieved by the use of analogues described herein.

The nucleoside analogues of this invention can also be used in any of the existing applications which use native nucleic acid probes labelled with haptens, fluorophores or other reporter groups, for example on Southern blots, dot blots and in polyacrylamide or agarose gel based methods or solution hybridization assays and other assays in microtitre plates or tubes or arrays of oligonucleotides or nucleic acids such as on microchips. The probes may be detected with antibodies targeted either against haptens which are attached to the base analogues or against the base analogues themselves which would be advantageous in avoiding additional chemical modification. Antibodies used in this way are normally labelled with a detectable group such as a fluorophore or an enzyme. Fluorescent detection may also be used if the base analogue itself is fluorescent or if there is a fluorophore attached to the nucleoside analogue.

The nucleoside analogues of the present invention with the combination of molecular diversity and increased numbers of positions where reporter groups may be added can result in a series of improved enzyme substrates.

Another preferred aspect of the invention is to incorporate the nucleoside analogue triphosphate into DNA by means of a polymerase but without a reporter label for the purpose of random mutagenesis. It has been shown by Zaccolo et al, 1996, J. Mol. Biol. 255, 589–603 that when nucleotide analogues with ambivalent base pairing potential are incorporated by the PCR into DNA products, they induce the formation of random mutations within the DNA products. In the above publication, the nucleotide analogue dPTP was shown to be incorporated into DNA by Taq polymerase in place of TTP and, with lower efficiency, dCTP. After 30 cycles of DNA amplification, the four transition mutations A→G, T→C, G→A and C→T were produced. The compound 8-oxodGTP was also used to cause the formation of the transversion mutations A→C and T→G. The nucleoside analogue triphosphates with ambivalent base pairing potential described within this invention may be used for a similar purpose.

RNA is an extremely versatile biological molecule. Experimental studies by several laboratories have shown that in vitro selection techniques can be employed to isolate short RNA molecules from RNA libraries that bind with high affinity and specificity to proteins, not normally associated with RNA binding, including a few antibodies, (Gold, Allen, Binkley, et al,1993, 497–510 in The RNA World, Cold Spring Harbor Press, Cold Spring Harbor N.Y., Gold, Polisky, Unlenbeck, and Yarus, 1995, Annu. Rev. Biochem. 64: 763–795, Tuerk and Gold, 1990, Science 249:505–510, Joyce, 1989, Gene 82:83–87, Szostak, 1992, Trends Biochem. Sci 17:89–93, Tsai, Kenan and Keene, 1992, PNAS 89:8864–8868, Tsai, Kenan and Keene, 1992, PNAS 89:8864–8868, Doudna, Cech and Sullenger, 1995, PNAS 92:2355–2359). Some of these RNA molecules have been proposed as drug candidates for the treatment of diseases like myasthenia gravis and several other auto-immune diseases.

The basic principle involves adding an RNA library to the protein or molecule of interest; washing to remove unbound RNA; then specifically eluting the RNA bound to the protein. This eluted RNA is then reverse transcribed and amplified by PCR. The DNA is then transcribed using modified nucleotides (either 2' modifications to give nuclease resistance e.g. 2' F, 2' NH₂, 2' OCH₃ and/or C5 modified pyrimidines and/or C8 modified pyrimidines). Those molecules that are found to bind the protein or other molecule of interest are cloned and sequenced to look for common ("consensus") sequences. This sequence is optimised to produce a short oligonucleotide which shows improved specific binding which may then be used as a therapeutic, or member of a binding pair.

The base analogues described here, when converted to the ribonucleoside triphosphate or ribonucleoside phosphoramidite, or to the deoxyribonucleoside triphosphate or deoxyribonucleoside phosphoramidite, will significantly increase the molecular diversity available for this selection process. This may lead to oligonucleotides with increased binding affinity to the target that is not available using the current building blocks.

The secondary structure of nucleic acids is also important when considering ribozyme function. The base analogues of the present invention may cause the formation of secondary structures which would otherwise be unavailable using native bases or other modified nucleotide derivatives.

The hybridization binding properties of nucleic acids incorporating base analogues of the present invention may have particular application in the antisense or antigene field.

The base analogues of the present invention may have properties which are different to those of the native bases and therefore are particularly suited to other important applications. In particular, the interaction of these base analogues with enzymes may be extremely important in vivo and may result in the development of new anti-viral therapeutics.

EXAMPLE 1

The synthesis of the novel tricyclic nucleoside analogue 9-(2'-deoxy-β-D-ribofuranosyl)-pyrrolo [4,3,2-de] pyrimido [4,5 -c] dihydro-oxazepine referred to as dS (1.13) and its 5'-triphosphate referred to as dSTP (1.14) is described.

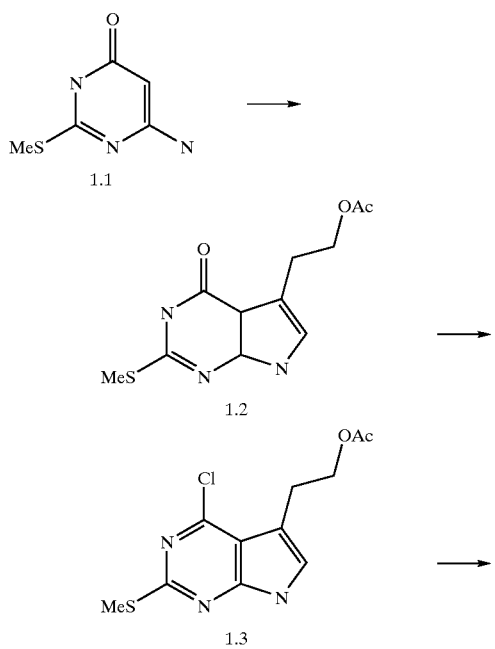

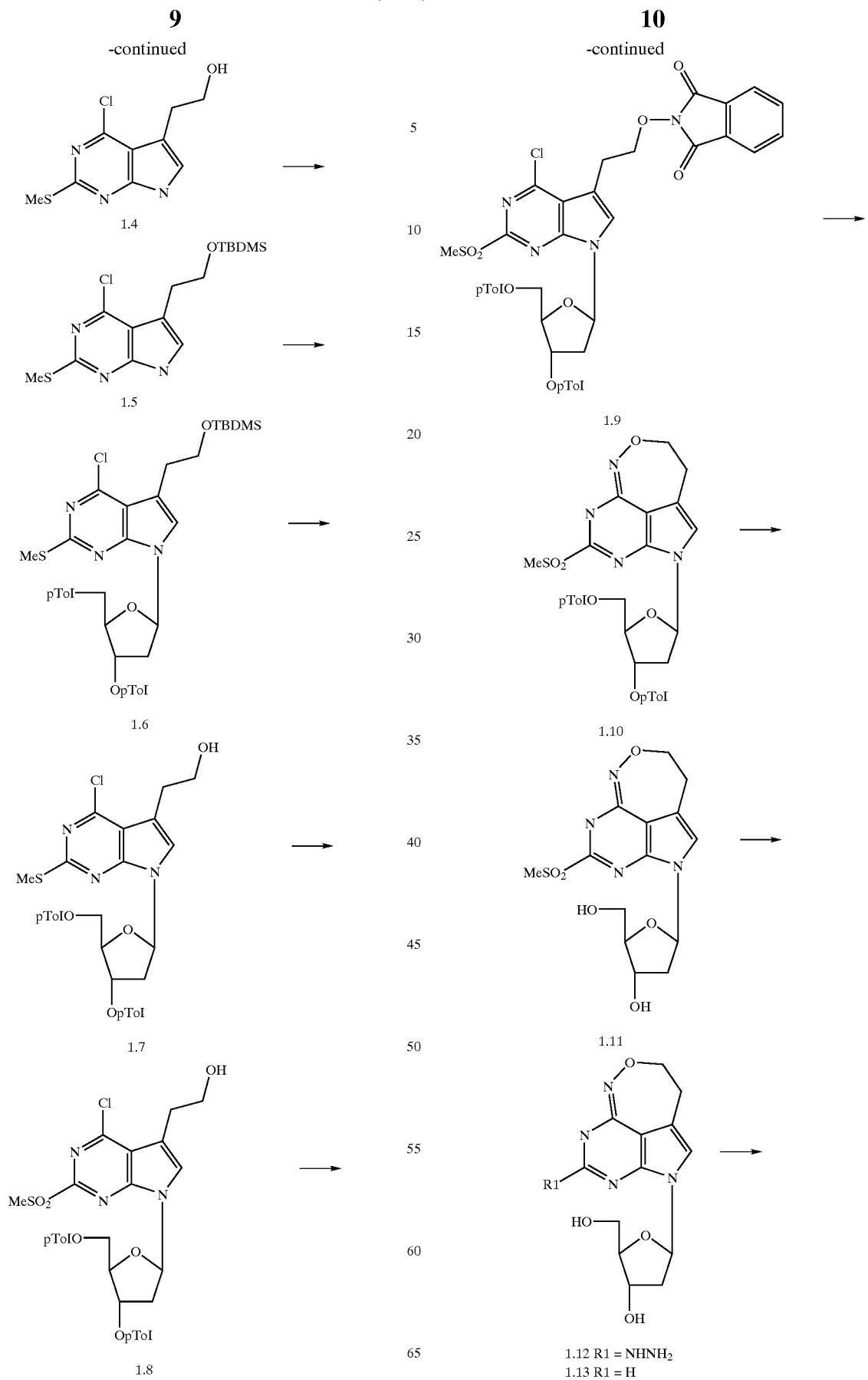

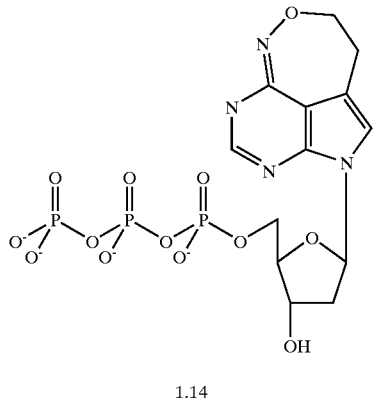

1.14

General 1H-nmr spectra were obtained on a Bruker DRX-300 spectrometer in d6-DMSO. Mass spectra were recorded on a Kratos MS890 instrument. Ultraviolet spectra were recorded on a Perkin Elmer Lambda 2 spectrophotometer in 10% aqueous methanol unless otherwise stated. Tlc was carried out on pre-coated F254 silica plates, and column chromatography with Merck Kieselgel 60. Melting points were measured on a Gallenkamp melting point apparatus (Fisons) and are uncorrected. Reactions were worked up as follows, unless otherwise stated. Reaction mixtures were evaporated to dryness and the product dissolved in chloroform and washed with saturated aqueous sodium bicarbonate solution. The organic fractions were combined and dried over anhydrous sodium sulphate, filtered and then evaporated to dryness.

2-Chloro4-acetoxybutan-1-al

To a solution of butane-1,4-diol (1.5 mmol) in pyridine (1 mmol) at 0° C. was added dropwise acetic anhydride (1 mmol), and the solution stirred at room temperature overnight. The solution was evaporated and dissolved in chloroform, washed sat. sodium bicarbonate, dried and evaporated to a clear liquid which was distilled to give the mono-acetate (76–84° C. @ 11 mbar).

To a solution of pyridinium chlorochromate (PCC) (24 g, 1.5 equiv.) in dichloromethane (200 ml) was added dropwise a solution of the alcohol (9.8 g) in dichloromethane (20 ml) and the solution stirred at room temperature for 1.5 hours. Ether (200 ml) was added and the solution filtered through florisil, and the residues washed with ether (3×200 ml). The ether solution was evaporated and then distilled to give the alcohol as a colourless liquid (48–52° C. @ 11 mbar).

To a solution of the aldehyde (11.39 g) in dry chloroform (100 ml) was added sulfuryl chloride (1.1 equiv. 7.7 ml) in chloroform (50 ml) dropwise and the solution stirred at room temperature overnight. The solution was evaporated, co-evaporated with toluene and the solution distilled to give the chloroaldehyde as a colourless liquid (69–74° C. @ 11 mbar).

5-(2-Acetoxyethyl)-2-methylsulfanyl-7H-pyrrolo[2,3-d]pyrimidin-4-one (1.2)

To a suspension of pyrimidine (1.1) (Johns and Baumann, J. Biol. Chem., (1913), 14, 384) (3 g, 19 mmol) and sodium acetate (3.3 g, 40 mmol) in water (100 ml) was added freshly prepared 2-chloro-4-acetoxybutan-1-al (4.7 g, 28.6 mmol) in three aliquots at two hourly intervals at 85° C. and then heating continued overnight. The solution was cooled, and the aqueous layer decanted and the product chromatographed (CHCl$_3$/5% MeOH) to give the product as a pale yellow solid. Yield 2.35 g, 46%. $\delta_H$ ([2H6]-DMSO) 11.99 (1 H, br s, NH), 11.53 (1 H, br s, NH), 6.73 (1 H, s, 6-H), 4.21 (2 H, t J 7.0 Hz, OCH$_2$), 2.91 (2 H, t J 7.0 Hz, OCH$_2$CH$_2$), 2.48 (3 H, s, CH$_3$S), 1.96 (3 H, s, CH$_3$CO) ppm. UV $\lambda_{max}$ (nm) 287 (13000), 224 (18100), $\lambda_{min}$ 245. pH 12 $\lambda_{max}$ 281 (12300).

5-(2-Acetoxyethyl)-4-chloro-2-methylsulfanyl-7H-pyrrolo[2,3-d]pyrimidine (1.3)

The above pyrrolopyrimidinone (1.2) (3.7 g, 13.8 mmol) was suspended in phosphoryl chloride (20 ml) and the solution heated at 45–50° C. overnight. The solution was cooled and poured onto ice and stirred for 10 mins and then neutralised with concentrated ammonia solution. The solid was filtered and recrystallised from methanol to give a yellow-brown solid which was chromatographed (CHCl$_3$/2% MeOH) to give the product as a pale brown solid, yield 1.3 g. Unreacted starting material was eluted from the column in CHCl$_3$/5% MeOH, yield 1.44 g. Overall yield 54%. $\delta_H$ ([2H6]-DMSO) 12.24 (1 H, br s, NH), 7.38 (1 H, s, 6-H), 4.26 (2 H, t J 6.8 Hz, OCH$_2$), 3.08 (2 H, t J 6.8 Hz, OCH$_2$CH$_2$), 2.52 (3 H, s, CH$_3$S), 1.98 (3 H, s, CH$_3$CO) ppm. UV $\lambda_{max}$ (nm) 314 (4800), 254 (28300), 222 (13000). pH 12 $\lambda_{max}$ 291 (5100), 257 (26700). Accurate mass measurement 285.0339, C$_{11}$H$_{12}$ClN$_3$O$_2$S requires 285.0356.

5-(2-Hydroxyethyl)4-chloro-2-methylsulfanyl-7H-pyrrolo[2,3-d]pyrimidine (1.4)

The above pyrrolopyrimidine (1.3) (2.14 g, 7.5 mmol) was suspended in 20 ml methanol and 0.880 ammonia (10 ml) added and the solution stirred at 40° C. overnight. The solvent was removed and the product suspended in methanol and filtered to give a pale yellow solid. Yield 0.71 g. A further 1.05 g was isolated by concentration of the mother liquors. Overall yield 1.76 g, 96%. $\delta_H$ 2.52 (3H, s, SCH$_3$), 2.91 (2H, t, J 7.1 Hz, OCH$_2$CH$_2$), 3.65 (2H, t, J 6.9 Hz, OCH$_2$), 4.68 (1H, t, OH), 7.27 (1H, s, H6), 12.12 (1H, s, NH) ppm.

4-Chloro-5-(2-t-Butyldimethylsilyloxyethyl)-2-methylsulfanyl-7H-pyrrolo[2,3-d]pyrimidine (1.5)

The hydroxyethyl pyrrolopyrimidine (1.4) (1.91 g, 7.8 mmol) was dissolved in DMF (25 ml) and tert-butyldimethylsilyl chloride (1.77 g, 11.7 mmol) and imidazole (1.6 g, 23.5 mmol) added and the solution stirred at room temperature for 6 hours. The solvent was removed and the product dissolved in chloroform, washed with water and the solvent evaporated. The product was precipitated by trituration with methanol, filtered and dried to give an off-white solid. A second fraction was obtained by concentration of the mother liquors. Yield 2.51 g, 89%. $\delta_H$ −0.07 (6H, s, 2×CH$_3$), 0.80 (9H, s, C(CH$_3$)$_3$), 2.52 (3H, s, SCH$_3$), 2.94 (2H, t, J 7.0 Hz, OCH$_2$CH$_2$), 3.78 (2H, t, J 7.0 Hz, OCH$_2$), 7.29 (1H, s, H6), 12.10 (1H, s, NH) ppm.

4-Chloro-5-(2-t-butyldimethylsilyloxyethyl)-2-methylsulfanyl-7-(3,5-di-O-p-toluoyl-2-deoxyribofuranosyl)-7H-pyrrolo[2,3-d]pyrimidine (1.6)

The above pyrrolopyrimidine (1.5) (3.3 g, 9.2 mmol) was suspended in acetonitrile (50 ml) and sodium hydride added (0.45 g, 11.2 mmol of 60%) and the solution stirred at room temperature for 30 minutes. To this was then added the chlorosugar (4.3 g, 11 mmol) and the solution stirred for a further 1.5 hours. The solution was evaporated and worked up as usual and the product was chromatographed (hexane/ether, 3:1) to give a white foam. Yield 5.56 g, 88%. $\delta_H$ −0.13 (6H. s, 2×SiCH$_3$), 0.74 (9H, s, C(CH$_3$)$_3$), 2.33 (3H, s, ArOCH$_3$), 2.37 (3H, 2, ArOCH$_3$), 2.55 (3H, s, SCH$_3$), 2.72–2.75 (1H, m, H2'), 2.84 (2H, t, J 6.6 Hz, OCH$_2$CH$_2$), 2.98–3.29 (1H, m, H2"), 3.71(2H, t, J 6.7 Hz, OCH$_2$), 4.45–4.61 (3H, m, H4', H5', H5"), 5.71–5.73 (1H, m, H3'), 6.67 (1H, t, J 7.0 Hz, H1'), 7.24–7.33 (4H, m, Ar), 7.46 (1H, s, H6), 7.80–7.93 (4H, m, Ar) ppm.

4-Chloro-5-(2-hydroxyethyl)-2-methylsulfanyl-7-(3, 5-di-O-p-toluoyl-2-deoxyribofuranosyl)-7H-pyrrolo [2,3-d]pyrimidine (1.7)

The nucleoside (1.6) (5.5 g, 8 mmol) was suspended in methanol (50 ml) and ammonium fluoride (3 g, 80 mmol) added and the solution heated at reflux for 3 hours. The solvent was evaporated and the product worked up as usual to give a foam which was chromatographed (CHCl$_3$/1% MeOH) to give the product as a white solid. Yield 3.98 g, 83%. $\delta_H$ 2.36 (3H, s, CH$_3$), 2.39 (3H, s, CH$_3$), 2.78–2.86 (1H, m, H2'), 2.85 (2H, t, J 6.9 Hz, OCH$_2$CH$_2$), 3.05–3.10 (1H, m, H2"), 3.33 (3H, s, SCH$_3$), 3.58–3.60 (2H, m, OCH$_2$), 4.55–4.59 (2H, m, H5', H5"), 4.73 (1H, t, OH), 4.61–4.69 (1H, m, H4'), 5.72–5.74 (1H, m, H3'), 6.65 (1H, t, J=7 Hz, H1'), 7.27–7.36 (4H, m, Ar), 7.49 (1H, s, H6), 7.81–7.95 (4H, m, Ar) ppm. UV $\lambda_{max}$ (nm) 252 (37000), 315, 285 (shoulder). pH 1, pH 12 $\lambda_{max}$ 257 (35200).

4-Chloro-5-(2-hydroxyethyl)-2-methylsulfonyl-7-(3, 5-di-O-p-toluoyl-2-deoxyribofuranosyl)-7H-pyrrolo [2,3-d]pyrimidine (1.8)

The sulfanyl derivative (1.7) (3.9 g, 6.5 mmol) was suspended in ethanol (300 ml) and to this was added magnesium monoperoxyphthalate (6.5 g, 13 mmol) in water (100 ml) and the solution stirred at 50° C. for 4 hours. The solution was then concentrated and worked up as usual to give a white foam which was chromatographed (CHCl$_3$ /1% MeOH) to give a white foam. Yield 3.90 g, 95%. M.p. 157–158° C. $\delta_H$ 2.36 (3H, s, ArOCH$_3$), 2.39 (3H, s, ArOCH$_3$), 2.78–2.86 (1H, m, H2'), 2.95 (2H, t, J=6.8 Hz, OCH$_2$CH$_2$), 3.11–3.16 (1H, m, H2"), 3.43 (3H, S, SO$_2$CH$_3$), 3.62 (2H, t, J 6.8 Hz, OCH$_2$), 4.49–4.68 (3H, m, H4', H5', H5"), 4.76 (1 H, t, OH), 5.76–5.78 (1H, m, H3'), 6.77 (1H, t, J 6.8 Hz, H1'), 7.26–7.37 (4H, m, Ar), 7.96 (1H, s, H6), 7.79–8.31 (4H, m, Ar) ppm. UV $\lambda_{max}$ (nm) 247 (42000), $\lambda_{min}$ 220 nm. pH 1 $\lambda_{max}$ 249 (36500). pH 12 $\lambda_{max}$243 (41300).

4-Chloro-5-(2-phthalimidooxyethyl)-2-methylsulfonyl-7-(3,5-di-O-p-toluoyl-2-deoxyribofuranosyl)-7H-pyrrolo [2,3-d]pyrimidine (1.9)

To a solution of the nucleoside (1.8) (3.67 g, 5.9 mmol), triphenylphosphine (2.3 g, 8.8 mmol) and N-hydroxyphthalimide (1.43 g, 8.8 mmol) in THF (50 ml) was added diethylazodicarboxylate (1.54 g, 8.8 mmol) and the solution stirred at room temperature overnight. The solution was evaporated and worked up as usual and the product chromatographed (CHCl$_3$/1% MeOH) to give a product which was recrystallised from ethanol to give a white solid. Yield 2.79 g, 62%. $\delta_H$ 2.28 (3H, s, ArCH$_3$), 2.38 (3H, s, ArCH$_3$), 2.85–2.91 (1H, m, H2'), 3.06–3.14 (1H, m, H2"), 3.27 (2H, t, J 6.6 Hz, OCH$_2$CH$_2$), 3.45 (3H, s, SO$_2$CH$_3$), 4.40 (2H, t, J=6.6 Hz, OCH$_2$), 4.51–4.56 (1H, m, H4'), 4.61–4.69 (2H, m, H5', H5"), 5.78–5.80(1H, m, H3'), 6.79 (1H, t, J 6.7 Hz, H1'), 7.16–7.36(4H, m, toluoyl), 7.72–8.00 (4H, m, toluoyl), 7.85 (4H, br. s, phthaloyl), 8.24 (1H, s, H6) ppm.

9-(3',5'-Di-O-p-toluoyl-2'-deoxyribofuranosyl)-2-methylsulfonyl-pyrrolo[4,3,2-de]pyrimido[4,5-c] dihydro-oxazepine (1.10)

To a solution of the phthalimido derivative (1.9) (2.4 g, 3.1 mmol) in acetonitrile (50 ml) was added anhydrous hydrazine (107 μl, 3.4 mmol) and the solution stirred at room temperature for 1 hour. The phthalic hydrazide was filtered off and washed with acetonitrile and then the solution was evaporated to dryness. The product was dissolved in ethanol (50 ml) and the solution heated at 75° C. overnight. The solution was evaporated and worked up as usual and the product chromatographed (ethyl acetate/hexane, 1:1) to give a white solid. Yield 0.63 g, 33%. Mp 173–174.5° C. $\delta_H$ 2.36 (3H, s, ArCH$_3$), 2.39 (3H, s, ArCH$_3$), 2.73–2.79 (1H, m H2'), 2.90 (2H, m, OCH$_2$CH$_2$), 3.03–3.09 (1H, m, H2"), 3.31 (3H, s, SO$_2$CH$_3$), 4.33 (2H, m, OCH$_2$), 4.47–4.56 (2H, m, H5', H5"), 4.62–4.66 (1H, m, H4'), 5.74–5.76 (1H, m, H3'), 6.69 (1 H, t, J 6.8 Hz, H1'), 7.29–7.38 (4H, m, Ar), 7.57 (1H, s, H6), 7.84–7.96 (4H, m, Ar), 11.52 (1H, NH) ppm. UV $\lambda_{max}$ (nm) 309 (8200), 238 (43000), $\lambda_{min}$ 225. pH 12 $\lambda_{max}$ 240, 287 (10300), 339 (4100).

9-(2'-Deoxyribofuranosyl)-2-methylsulfonyl-3-allyl-pyrrolo[4,3,2-de]pyrimido [4,5-c]dihydro-oxazepine (1.11)

The tricyclic nucleoside (1.10) (0.63 g, 1.04 mmol) was dissolved in methanolic ammonia (25 ml) and stirred at room temperature overnight. The solvent was removed and the product chromatographed (CHCl$_3$/10% MeOH) to give an off-white powder. Yield 0.28 g, 80%. $\delta_H$ 2.20–2.24 (1H, m, H2'), 2.49–2.53 (1H, m, H2"), 2.98 (2H, t, J 4.8 Hz, OCH$_2$CH$_2$), 3.28 (3H, s, SO$_2$CH$_3$), 3.47–3.55 (2H, m, H5', H5"), 3.82–3.83 (1H, m, H4'), 4.35 (3H, br. s, H3', OCH$_2$), 4.90 (1H, t, 5'-OH), 5.33 (1H, d, 3'-OH), 6.57 (1H, t, J 7.0 Hz, H1'), 7.62 (1H, s, H6), 11.43 (1H, s, NH) ppm. UV $\lambda_{max}$ (nm) 313 (5300), 280 (shoulder), 232 (18800), $\lambda_{min}$ 255. pH 12 $\lambda_{max}$ 313 (5400), 287 (5100), 232 (18900). pH 1 $\lambda_{max}$ 338 (3500), 9-(2'-Deoxyribofuranosyl)-pyrrolo[4,3,2-de] pyrimido[4,5-c]dihydro-oxazepine (1.13)

The deprotected tricyclic nucleoside (1.11) (270 mg, 0.8 mmol) was dissolved in ethanol (15 ml) and to this was added hydrazine (0.5 ml) and the solution heated at reflux under nitrogen in a sealed bottle for 24 hours. The solvent was then removed and the product (1.12) redissolved in water (10 ml) and mercury II oxide (0.86 g, 4 mmol) added in 4 portions over 1 hour at 95° C., and then the solution heated at reflux for a further 2 hours. The reaction was cooled, diluted with water and hydrogen sulfide gas bubbled into the solution for two minutes. The solution was then filtered through celite and the filtrate evaporated and then chromatographed (CHCl$_3$/10% MeOH) to give the product (1.13) as a pale yellow solid. Yield 31 mg, 13%. $\delta_H$ 2.10–2.19 (1H, m, H2'), 2.43–2.55 (1H, m, H2"), 2.90–2.99 (2H, m, OCH$_2$CH$_2$), 3.41–3.57 (2H, m, H5', H5"), 3.79–3.82 (1H, m, H4'), 4.29–4.34 (3H, m, H3', OCH$_2$), 4.99 (1H, t, 5'-OH), 5.27 (1H, d, 3'-OH), 6.55 (1H, t, J 7.0 Hz, H1'), 7.36 (1H, s, H6), 8.20 (1H, s, H2), 10.65 (1H, s, NH) ppm. UV $\lambda_{max}$ (nm) 286 (5000), $\mu_{min}$ 255. pH 1 $\lambda_{max}$ 290 (5850), 290 (9800), $\lambda_{min}$ 260. pH 12 $\lambda_{max}$ 290 (8700), $\lambda_{min}$ 250. $\epsilon_{260}$ ($\mu$M)=2.9, $\epsilon_{280}$ ($\mu$M)=4.7.

9-(2'-Deoxy-5'-O-triphosphate-ribofuranosyl)-pyrrolo[4,3,2-de]pyrimido[4,5-c]dihydro-oxazepine (dSTP) (1.14)

The 5'-triphosphate of compound (1.13) was synthesised by analogous methods to those described in example (4.11). $\delta_P$ (D$_2$O); −5.85 (d, γ-P), −10.71 (d, α-P), −22.04 (t, β-P) ppm.

EXAMPLE 2

The synthesis of the novel tricyclic nucleoside analogue 9-(2-deoxy-β-D-ribofuranosyl)-pyrrolo [4,3,2-de]pyrimido [4,5 -c]dihydro-oxazepine, 2.13 is described. 2.13 is the same compound as 1.13. This example describes an earlier preparation.

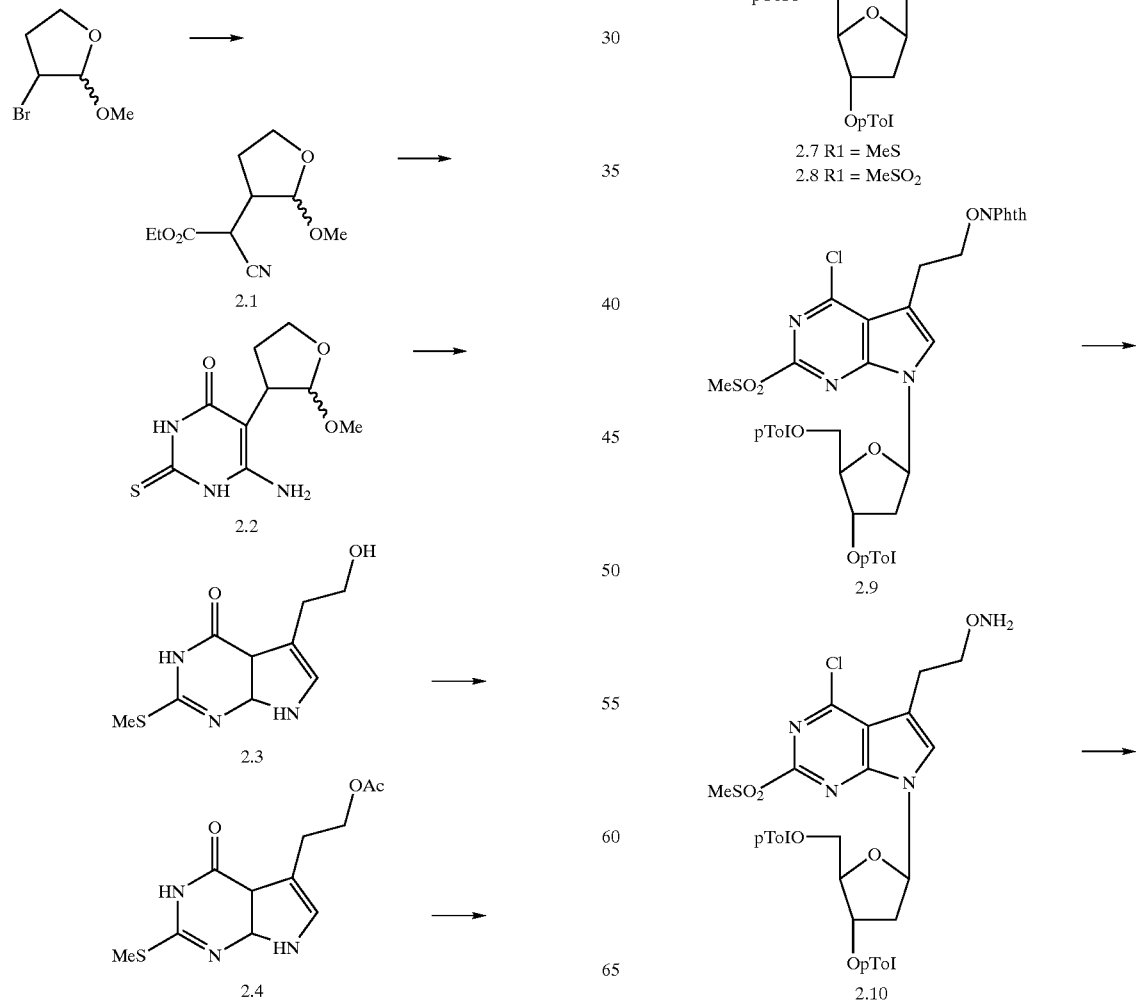

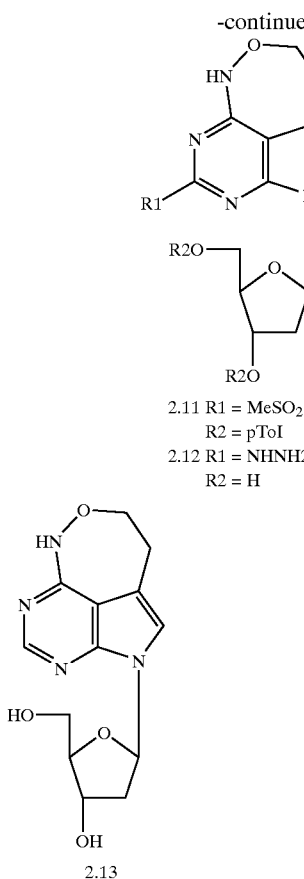

2.11 R1 = MeSO$_2$
R2 = pTol
2.12 R1 = NHNH2
R2 = H 2.13

$^1$H-NMR spectra were recorded at 250.13 MHz or at 300.13 MHz or on a on a Bruker WM 250 or AM300 spectrometer with tetramethylsilane as the external standard (J values in Hz). D$_2$O was added to $^1$H NMR samples for the identification of exchangeable protons. UV spectra were obtained using a Perkin Elmer Lambda 2 spectrophotometer, all samples being dissolved in distilled water or analytical methanol (Aldrich). Mass spectra were recorded on a Kratos MS890 instrument. Melting points are uncorrected.

Anhydrous DMF was obtained from Aldrich. Pyridine and acetonitrile (Rathburn) were dried by refluxing over calcium hydride followed by distillation. THF (Merck) and dioxan (Merck) were dried by reflux and distillation from sodium and benzophenone. All other reagents were obtained from Aldrich. Silica gel column chromatography used either Kieselgel 60 (<63 μm) or Kieselgel 60 H (where indicated) from Merck. Precoated silica gel F$_{254}$ plates for preparative (1 mm) or thin-layer chromatography (TLC) (Merck) were developed using one of the following solvent systems; A, ethyl acetate: cyclohexane (1:2); B, MeOH:CHCl$_3$ 1:9; C, MeOH:CHCl$_3$ 2:8; D, MeOH:CHCl$_3$ 15:85; E, MeOH:CHCl$_3$ 2;98; F, MeOH:CHCl$_3$ 5:95. Tetrahydrofuranosyl derivatives were identified with anisaldehyde solution which contained anisaldehyde (9.2 ml), acetic acid (3.75 ml), conc. H$_2$SO$_4$ (1.25 ml) and 95% ethanol (388 ml).

Ethyl-2-cyano-2-(2-methoxytetrahydrofuran-3-yl) acetate 2.1

Sodium hydride (95%, 30.32 g, 1.2 mol) was suspended in anhydrous DMF (350 ml) in a 2 L, 3-necked flask and ethyl cyanoacetate (136 ml, 1.2 mol) was added dropwise with stirring under argon over 1 h. After a further 15 min, 3-bromo-2-methoxytetrahydrofuran (75 g, 0.41 mol) was added, followed by sodium iodide (2 g) and then the solution was heated with vigorous stirring at 140° C. for 20 h under argon. After cooling, water (200 ml) was added and the solution was concentrated on a rotary evaporator to about 300 ml. More water (200 ml) was added and the crude product was extracted into diethylether (4×500 ml). The combined extracts were dried (Na$_2$SO$_4$), filtered and evaporated. Distillation of the residue under reduced pressure through a Vigreaux column afforded a colourless liquid (13.28 g, 15%). The cut b. p. 90–110° C./0.4 mmHg was taken; R$_f$(in A), 0.45, 0.36; stains yellow with anisaldehyde/H$^+$; δ$_H$(d$^6$-DMSO) 5.00 (0.75 H, m, mixt. of trans-2-H), 4.89 (0.25 H, d J2.1, cis-2-H), 4.29–4.19 (2 H, 2 q, cis/trans-CH$_2$), 4.06–3.83 (2 H, 2 m, cis/trans-5-H), 3.39 (0.75 H, s, MeO), 3.36 (0.75 H, s, MeO), 3.35 (0.75 H, s, MeO), 3.31 (0.75 H, s, MeO), 2.78–2.70 (1 H, m, cis/trans-3-H), 2.30–1.71 (2 H, 2 m, 2×cis/trans-4-H) ppm; m/z (EI) 213.1002 (M$^+$; Calc. for C$_{10}$H$_{15}$NO$_4$, 213.1023).

6-Amino-2-thio-5-(2-methoxytetrahydrofuran-3-yl) pyrimidin-4-one 2.2

To a solution of thiourea (15 g, 197 mmol) in absolute ethanol (400 ml) was added 1 M sodium ethoxide solution in ethanol (196 ml, 196 mmol), followed by a solution of 2.1 (37.28 g, 175 mmol) in absolute ethanol (100 ml). The mixture was heated at reflux for 3 h and then evaporated to a foam. The residue was redissolved in water (150 ml) and extracted with diethylether (50 ml). The aqueous layer was neutralised with 50% aq. acetic acid, and after a short time at 4° C., a pale brown solid (19.98 g) precipitated. After concentration and chilling, a further crop (2.76 g) was obtained. Yield, 22.74 g, 54%. Crystallisation from ethanol gave white needles, mp >300° C. (darkens 205° C.)(Found: C, 44.3; H, 5.4; N, 17.4. C$_9$H$_{13}$N$_3$SO$_3$ requires C, 44.4; H, 5.4; N,17.3); R$_f$(in B), 0.45 & 0.39 (2 diastereomers)-stains red with anisaldehyde/H$^+$; δ$_H$(d$^6$-DMSO) 11.76 (1 H, br s, NH), 11.46 (1 H, br s, NH), 6.22 (0.26 H, br s, 6a-NH$_2$), 6.06 (1.74 H, s, 6b-NH$_2$), 5.05 (0.13 H, d, J 3.4, 2'-Ha), 4.80 (0.87 H, d, J 4.7, 2'-Hb), 3.94–3.80 (3 H, m, 3'-H and 2×5'-H) 3.33 (0.39 H, s, a-MeO), 3.21 (2.61 H, s, b-MeO), 2.50 (1 H, m, 4'-H), 1.70 (1 H, m, 4'-H) ppm; λ$_{max}$(MeOH)/nm 203 (25 200), 282 (18 800).

5-(2-Hydroxyethyl)-2-methylsulfanyl-7H-pyrrolo[2,3-d]pyrimidin-4-one 2.3

To a solution of 2.2 (14.85 g, 61 mmol) in anhydrous DMF (100 ml) was added methyl iodide (4.06 ml, 65 mmol) and the reaction mixture stirred for 6 h at room temp. Evaporation. and trituration of the residue with diethylether (3×250 ml) gave a pale yellow solid (11.20 g, 82%). Crystallisation from ethanol gave white needles, mp 237–238° C. (Found: C, 46.1; H, 5.2; N, 18.4. C$_9$H$_{11}$N$_3$O$_2$S.0.5H$_2$O requires C, 46.1; H, 5.2; N, 18.0); R$_f$ (in B), 0.33-becomes pink/purple on plate under uv; δ$_H$ (d$^6$-DMSO) 11.88 (1 H, br s, NH), 11.39 (1 H, br s, NH), 6.65 (1 H, d J1.5, 6-H), 4.51 (1 H, t J5.3, OH), 3.58 (1 H, m, OCH$_2$), 2.79 (1 H, t J7.2, OCH$_2$CH$_2$), 2.48 (3 H, s, CH$_3$S);

5-(2-Acetoxyethyl)-2-methylsulfanyl-7H-pyrrolo[2,3-d]pyrimidin-4-one 2.4

Compound 2.3 (11.25 g, 50 mmol) was suspended in dry pyridine (500 ml) and acetic anhydride (8 ml, 85 mmol) was added. The mixture was stirred overnight at room temperature in the dark. Evaporation and coevaporation of residual pyridine with water, followed by recrystallisation from acetone:water (9:1) gave white needles (7.88 g, 59%); $R_f$ (in B), 0.56; $\delta_H$(d$^6$-DMSO) 11.99 (1 H, br s, NH), 11.53 (1 H, br s, NH), 6.73 (1 H, s, 6-H), 4.21 (2 H, t J7.0, OCH$_2$), 2.91 (2 H, t J7.0 , OCH$_2$CH$_2$), 2.48 (3H, s, CH$_3$S), 1.96 (3H, s, CH$_3$CO); $\lambda_{max}$(MeOH)/nm 221, 287; m/z (EI) 267.0674 (M$^+$; Calc. for C$_{11}$H$_{13}$N$_3$O$_3$S, 267.0696).

5-(2-Acetoxyethyl)-4-chloro-2-methylsulfanyl-7H-pyrrolo[2,3-d]pyrimidine 2.5

Compound 2.4 (3.2 g, 12 mmol) and benzyltriethylammonium chloride (5.1 g, 24 mmol) were dried in a vacuum oven at 70+ C. over P$_2$O$_5$ overnight then suspended in dry acetonitrile (65 ml). Dry dimethylaniline (2.13 ml, 12 mmol) was added followed by freshly distilled phosphoryl chloride (6.75 ml, 72 mmol). The mixture was heated at reflux for 1.5 h and the excess phosphoryl chloride removed by distillation. The resulting gum was added to crushed ice and after 0.5 h the mixture was extracted with chloroform (500 ml). The organic phase was washed with saturated aq. sodium hydrogen carbonate (50 ml), dried (Na$_2$SO$_4$) and evaporated. Silica gel column chromatography (52×400 mm) with chloroform as the eluent afforded a white solid, (992 mg, 29%); $R_f$ (in F), 0.65; $\delta_H$ (d$^6$-DMSO) 12.24 (1 H, br s, NH), 7.38 (1 H, s, 6-H), 4.26 (2 H, t J 6.8, OCH$_2$), 3.08 (2 H, t J 6.8, OCH$_2$CH$_2$), 2.52 (3 H, s, CH$_3$S), 1.98 (3 H, s, CH$_3$CO); $\lambda_{max}$(MeOH)/nm 221, 252, 311; m/z (EI) 285.0339 (M$^+$; Calc. for C$_{11}$H$_{12}$ClN$_3$O$_2$S, 285.0356).

5-(2-tert-Butyldimethylsilyloxyethyl)-4-chloro-2-methylsulfanyl-7H-pyrrolo[2,3-d]pyrimidine 2.6

5-(2-Acetoxyethyl)-4-chloro-2-methylsulfanyl-7H-pyrrolo[2,3-d]pyrimidine 2.5 (750 mg, 1.66 mmol) was de-acetylated with methanol-aq ammonia (100 ml) and dried by co-evaporation with dry pyridine. The residue was dissolved in dry pyridine (80 ml) and tert-butyldimethylsilyl chloride (598 mg, 3.94 mmol) added. The solution was stirred overnight, evaporated, and residual pyridine removed by co-evaporation with water (2×20 ml). The residue was dissolved in chloroform (500 ml), washed with saturated aq. sodium bicarbonate solution (100 ml), dried (Na$_2$SO$_4$) and evaporated. The crude product was purified by silica gel chomatography (32×400 mm) eluting with chloroform to give a white solid, 826 mg, 88%. $R_f$ (in C) 0.43; $\delta_H$(d$^6$-DMSO) 12.10 (1 H, br s, NH), 7.28 (1 H, s, 6-H), 3.81 (2 H, t J 7.0, O—CH$_2$), 2.96 (2 H, t J 7.0, O—CH$_2$CH$_2$), 2.53 (3 H, s, CH$_3$), 0.83 (9 H, s, 3×CH$_3$), −0.05 (6 H, s, 2×CH$_3$).

4-Chloro-5-hydroxyethyl-2-methylsulfanyl-7-(3,5-di-O-p-toluoyl-2-deoxy-β-D-ribofuranosyl)-7H-pyrrolo[2,3-d]pyrimidine 2.7

Compound 2.6 (5.86 g, 16.4 mmol) in dry acetonitrile (200 ml) was treated with NaH (60% in oil, 720 mg, 18 mmol) and chlorohalogenose (8.94 g, 23 mmol) was added. Purification by silica gel chromatography (32×300 mm) eluting with dichloromethane gave the TBDMS-protected nucleoside as a white foam. $R_f$ (in C), 0.8; (in D) 0.86. This was then desilylated with ammonium fluoride (6.07 g, 164 mmol) in methanol (500 ml). Purification by silica gel chomatography (32×180 mm) eluting with chloroform gave a white foam, 7.15 g, 73%; $R_f$ (in D) 0.29; $\delta_H$(d$^6$-DMSO) 7.98 (2 H, d J8.2, 2 to IH), 7.93 (2 H, d J8.2, 2 to IH), 7.29 (2 H, d J8.2, 2 to IH), 7.26 (2 H, d J8.2, 2 to IH), 7.23 (1 H, s, 6-H), 6.77 (1 H, t J7.0, 1'-H), 5.74 (1 H, m, 3'-H), 4.77–4.71 (1 H, m, 4'-H), 4.63 (1 H, t J5.0, OH), 4.59–4.55 (2 H, m, 2×5'-H), 3.63 (2 H, m, CH$_2$O), 3.43 (3 H, s, CH$_3$SO$_2$), 3.17–3.07 (1 H, m, 2'-H), 2.96 (2 H, t J6.9, OCH$_2$CH$_2$), 2.86–2.78 (1 H, m, 2'-H), 2.39 (3 H, s, tol CH$_3$), 2.36 (3H, s, tol CH$_3$).

4-Chloro-5-hydroxyethyl-2-methylsulfonyl-7-(3,5-di-O-p-toluoyl-2-deoxy-β-D-ribofuranosyl)-7H-pyrrolo[2,3-d]pyrimidine 2.8

To compound 2.7 (5.96 g, 10 mmol) in ethanol (800 ml) was added magnesium monoperoxyphthalate (9.90 g, 20 mmol) in water (200 ml) and the solution stirred at 50° C. for 4 h. The reaction mixture was then concentrated and the residue partitioned between chloroform (500 ml) and saturated aq. sodium bicarbonate solution (500 ml). The aqueous phase was re-extracted with chloroform (500 ml) and the combined organic phase dried (Na$_2$SO$_4$) and evaporated to give a white foam (5.34 g, 8.50 mmol, 85%); mp 157–158° C.; $R_f$ (in F), 0.17—fluorescent; $\delta_H$(d$^6$-DMSO) 7.99 (1 H, s, 6-H), 7.95 (2 H, d J8.2, 2 to IH), 7.81 (2 H, d J8.2, 2 to IH), 7.36 (2 H, d J8.2, 2 to IH), 7.28 (2 H, d J8.2, 2 to IH), 6.77 (1 H, t J7.0, 1'-H), 5.77 (1 H, m, 3'-H), 4.76 (1 H, t J5.0, OH), 4.68–4.49 (3 H, m, 4'-H, 2×5'-H), 3.63 (2 H, m, CH$_2$O), 3.43 (3 H, s, CH$_3$SO$_2$), 3.17–3.07 (1 H, m, 2'-H), 2.96 (2 H, t J6.9, OCH$_2$CH$_2$), 2.86–2.78 (1 H, m, 2'-H), 2.39 (3 H, s, tol CH$_3$), 2.36 (3 H, s, tol CH$_3$).

4-Chloro-5-phthalimidooxyethyl-2-methylsulfonyl-7-(3,5-di-O-p-toluoyl-2-deoxy-β-D-ribofuranosyl)-7H-pyrrolo[2,3-d]pyrimidine 2.9

Compound 2.8 (7.54 g, 12 mmol) was suspended in dry THF (500 ml) containing triphenylphosphine (4.72 g, 18 mmol) and N-hydroxyphthalimide (2.92 g, 18 mmol). Diethylazodicarboxylate (2.83 ml, 18 mmol) was then added and the solution stirred for 1.5 h at room temp. After this time the product was worked-up. Purification by silica gel chomatography (44×400 mm). eluting with chloroform, followed by crystallisation from ethanol gave white needles (7.17 g, 78%); $R_f$ (in D), 0.89; $\delta_H$(d$^6$-DMSO) 8.25 (1 H, s, 6-H), 7.96 (2 H, d J8.2, 2 to IH), 7.86 (4 H, s, 4 phth H), 7.75 (2 H, d J8.2, 2 to IH), 7.37 (2 H, d J8.2, 2 to IH), 7.19 (2 H, d J8.2, 2 to IH), 6.79 (1 H, t J6.9, 1'-H), 5.80 (1 H, m, 3'-H), 4.67–4.50 (3 H, m, 4'-H, 2×5'-H), 4.40 (2 H, m, CH$_2$O), 3.45 (3 H, s, CH$_3$SO$_2$), 3.28 (2 H, t J6.6, OCH$_2$CH$_2$), 3.17–3.07 (1 H, m, 2'-H), 2.86–2.78 (1 H, m, 2'-H), 2.39 (3 H, s, tol CH$_3$), 2.36 (3 H, s, tol CH$_3$).

9-(3,5-Di-O-p-toluoyl-2-deoxy-β-D-ribofuranosyl)-2-methylsulfonyl-pyrrolo[4,3,2-de]pyrimido[4,5-c]dihydro-oxazepine 2.11

Compound 2.9 (6.53 g, 8.5 mmol) was stirred in a solution of saturated ammonia in dry dioxan (100 ml) in a sealed bottle at room temp. for 5 h. Compound 2.10 was detected on TLC as a slower running component $R_f$ (in D), 0.21. The solution was then evaporated to dryness and the residue refluxed in absolute ethanol (500 ml) for 24 h. Evaporation, followed by silica gel chomatography (42×350 mm) in chloroform and crystallisation from ethanol gave white needles (2.08 g, 41%); mp 173–174.5° C.; $R_f$ (in E), 0.79; $\delta_H$(d$^6$-DMSO) 11.52 (1 H, br s, NH), 7.95 (2 H, d J8.2, 2 to IH), 7.85 (2 H, d J8.2, 2 to IH), 7.56 (1 H, s, 6-H), 7.36 (2 H, d J8.2, 2 to IH), 7.30 (2 H, d J8.2, 2 to IH), 6.79 (1 H, t J7.0, 1'-H), 5.75 (1 H, m, 3'-H), 4.66–4.47 (3 H, m, 4'-H, 2×5'-H), 4.34 (2 H, m, CH$_2$O), 3.32 (3 H, s, CH$_3$SO$_2$), 3.10–3.00 (IH, m, 2'-H); 2.90 (2 H, m, OCH$_2$CH$_2$), 2.79–2.73 (1 H, m, 2'-H), 2.39 (3 H, s, tol CH$_3$), 2.36 (3 H, s, tol CH$_3$).

9-(2-Deoxy-β-D-ribofuranosyl)-pyrrolo[4,3,2-de]pyrimido[4,5-c]dihydro-oxazepine 2.13

Compound 2.11 (607 mg, 1 mmol) was heated in a sealed bottle with anhydrous hydrazine (2 ml) in dry ethanol (25 ml) at 100° C. for 24 h. The solution was then evaporated and residual hydrazine removed by co-evaporation with water to give the crude hydrazino derivative 2.12 (streaks from baseline on silica TLC, solvent E). The residue was then heated to reflux in 25% aqueous ethanol (30 ml) and mercury (II) oxide (217 mg, 10 mmol) added in four portions over 1 h. After heating at reflux for a further 2 h, the reaction mixture was filtered though celite and the filtered material washed with hot ethanol (100 ml). The combined filtrates were evaporated and the residue purified twice by silica gel chomatography (32×150 mm) eluting with a gradient of 0–3% methanol in chloroform. A pale brown solid 2.13 (73 mg, 25%) was obtained. $R_f$ (in E), 0.13.

EXAMPLE 3

The synthesis of the analogue of compound (1.7) containing an azido functional group (3.8) to allow introduction of a reporter moiety is described. The azide group can then be reduced using triphenyl phosphine and water to provide the free primary amine (Mag et al, 1989, Nucleic Acids Research 17, 5973–5988). This provides a means of incorporating a reactive group such as $NH_2$. The primary amine generated can either be protected with a suitable protecting group such as monomethoxy trityl or reacted with an active ester of a hapten containing molecule such as the N-hydroxysuccinimidyl ester of 2,4-dinitrophenyl acetic acid. The secondary alcohol remaining can then be converted to its hydroxyphthalimide derivative according to the reaction conditions in example 1.9. The formation of the corresponding tricyclic derivative can then be achieved by carrying out the subsequent synthetic steps illustrated in example 1. The tricyclic derivative thus obtained can be hapten derivatised or have a reactive group attached as previously described in the term signal moiety. By having the amine protected the signal moiety can either be added at the triphosphate stage or after the nucleotide has been incorporated into an oligomer.

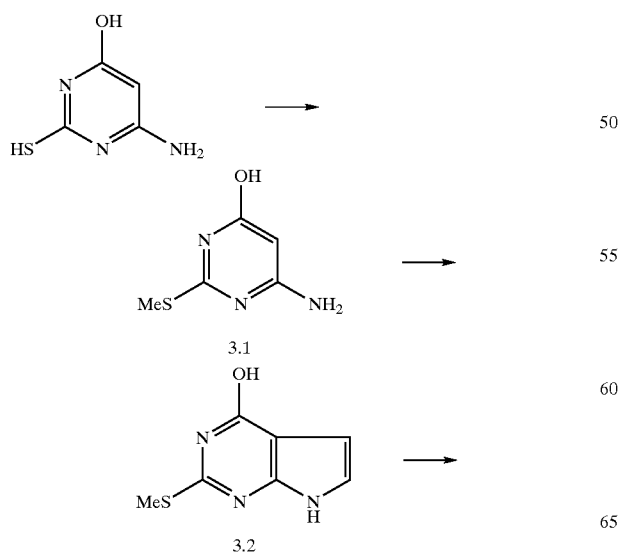

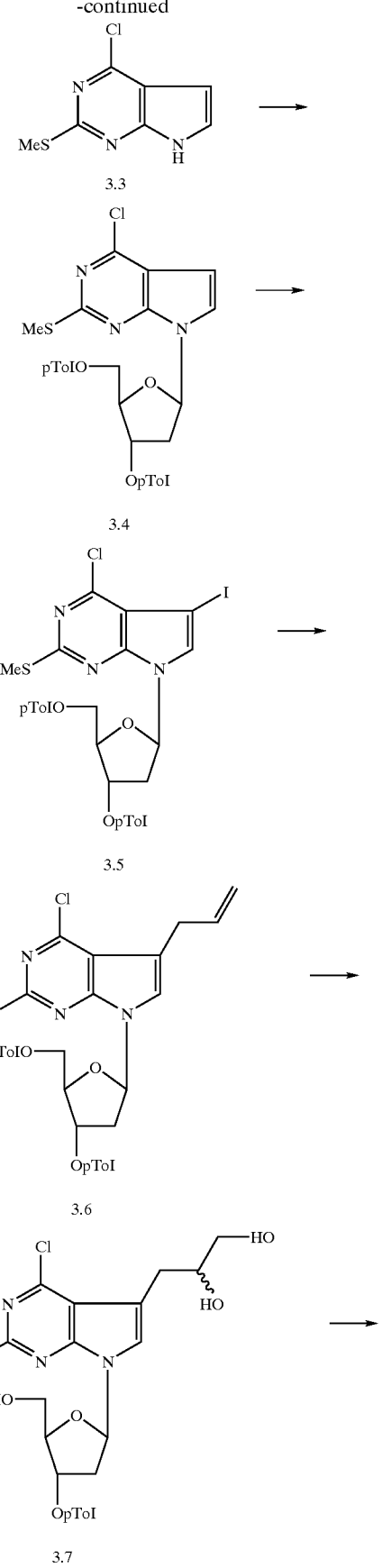

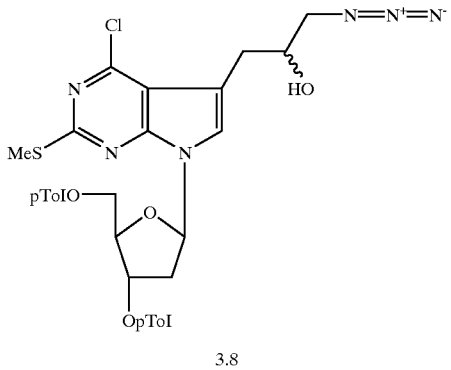

3.8

General

All reagents and materials were supplied by Sigma, Aldrich or Fluka unless stated. NMR experiments were carried out using a JEOL JNM LA300 FT nmr system, electrospray mass spectra were recorded on a Finnigan Navigator platform using Masslab 2.0 software. HPLC was performed using a Waters 600 pump and controller in conjunction with a Waters 996 photodiode array detector and Millenium 2010 software. Reverse phase HPLC was performed using a Hamilton PRP1 C18 reverse phase column (7×305 mm). TLC analyses were performed on Merck silca gel 60 $F_{254}$ tlc plates, with visualisation of products by UV excitation (254 nm), ninhydrin/EtOH solution (2% w/v), $KMnO_4/H_2SO_4/H_2O$ (10/1/100 w/v/v) or anisaldehyde solution (anisaldehyde/$H_2SO_4$/EtOH 5/1/50 v/v/v).

2-(Methylthio)-4-hydroxy-6-aminopyrimidine (3.1)

Prepared from 2-mercapto-4-amino-6-hydroxypyrimidine monohydrate using the method of J. Davoll (*J. Chem. Soc.,* (1960), 131). The product (3.1) was used directly in the next reaction without complete drying.

2-(methylthio)-4-hydroxy-pyrrolo[2,3]pyrimidine (3.2)

2-(Methylthio)4-hydroxy-6-aminopyrimidine (3.1) (40 g) and sodium acetate (40 g, 2 eq.) were mixed with water (600 ml) and the slurry heated to 80° C. with vigorous stirring. To the mixture was then added chloroacetaldehyde (50 wt. % in water, 40 g, 1 eq.), slowly over 10 mins. The mixture turned yellow in colour and the solid mostly dissolved, before a new solid precipitated. After a further 30 mins, the mixture was allowed to cool overnight, then the solid was collected by filtration, washed well with water and then with acetone. Dried under vacuum at 50° C. to give (3.2), 8.7 g. $\delta_H$ (300MHz, DMSO-$d_6$); 2.49 (3H, s, $SCH_3$), 6.33 (1H, m, H7), 6.89 (1H, m, H8), 11.74 and 12.03 (2×broad s, $D_2O$ exch.) ppm.

2-(Methylthio)4-chloro-pyrrolo[2,3]pyrimidine (3.3)

Compound (3.2) (8.7 g, 48 mmol) was mixed with phosphorus oxychloride (350 ml) and N,N-diethylaniline (17.5 ml). This mixture was heated under reflux for 4 hrs; the brown solution was then concentrated under reduced pressure. The residual oil was treated with an ice-water mixture and stirred until the ice had melted. The resultant mixture was extracted repeatedly with ether until no more UV-active material was being extracted, the combined aqueous extracts were dried ($MgSO_4$), filtered and evaporated to a light beige solid. Dried under vacuum at 50° C. to give (3.3), 7.3 g (76%). $\delta_H$ (300 MHz, DMSO-$d_6$) 1.78 (3H, s, $SCH_3$), 5.70 (1 H, d, J 3.7 Hz, H7) and 6.51 (1H, d, J 3.7 Hz, H8) ppm.

2-(Methylthio)-4-chloro-7-(2'-deoxy-3',5'-di-O-p-toluoyl-β-D-ribofuranosyl)pyrrolo[2,3d]pyrimidine (3.4)

Prepared according to literature methods (Z. Kazimierczuk, H. B. Cottam, G. R. Revankar & R. K. Robins; *J. Am. Chem. Soc.,* (1984), 106, 6379–6382). Compound (3.3) (5.9 g, 29.6 mmol) gave 7.52 g (46%) of compound (3.4) after recrystallisation from ethanol. $^1$H-nmr data matched reported values.

2-(Methylthio)-4-chloro-5-iodo-7-(2'-deoxy-3',5'-di-O-p-toluoyl-β-D-ribofuranosyl)pyrrolo[2,3d]pyrimidine (3.5)

Prepared according to literature methods (C. A. Buhr, R. W. Wagner, D. Grant & B. C. Froehler; *Nucleic Acids Research,* (1996), 24, 2974–2980). Compound (3.4) (7.5 g, 13.6 mmol) gave 8.33 g (90%) of (3.5). $^1$H-nmr data matched reported values.

2-(Methylthio)-4-chloro-5-allyl-7-(2'-deoxy-3',5'-di-O-R-toluoyl-β-D-ribofuranosyl)pyrrolo[2,3d]pyrimidine (3.6)

Compound (3.5) (8.13 g, 12 mmol) was mixed with anhydrous toluene (60 ml) in an oven-dried flask. To this was then added allyltributyltin (7.95 g, 24 mmol) and bis(triphenylphosphine) palladium (II) dichloride (0.42 g, 0.6 mmol). The resulting mixture was heated at reflux under argon atmosphere for 3 days, then it was cooled, filtered through Celite filter-aid, and concentrated under reduced pressure. The residue was redissolved in chloroform and washed twice with water, then dried ($MgSO_4$), filtered and concentrated under reduced pressure. The residue was triturated with ether, 1: petroleum spirit, 1; the resulting solid was collected by filtration, washed with ether and dried to give (3.6), 2.06 g. The trituration residues were purified by flash column chromatography (silica. 0–5% methanol in chloroform) to give a further 1.56 g. Total yield=3.62 g (51%) of (3.6). $\delta_H$ ($CDCl_3$) 2.43+2.25 (each 3H, s, toluoyl $CH_3$), 2.63 (3H, s, $CH_3S$), 2.5–2.9 (2H, m, 2'-$H_{a,b}$), 3.47 (2H, m, allyl —$CH_2$—), 4.54–4.77 (3H, m, 5'-$H_2$+4'-H), 4.93–5.03 (2H, m, allyl =$CH_2$), 5.74 (1H, m, 3'-H), 5.79–5.92 (1H, m, allyl =CH—), 6.76 (1H, m, 1'-H), 6.94 (1H, s, $C_6$—H), 7.20–7.30 and 7.89–8.00 (each 4H, toluoyl aryl-H) ppm.

2-(Methylthio)-4-chloro-5-(2,3-dihydroxypropyl)-7-(2'-deoxy-3',5'-di-O-p-toluoyl-β-D-ribofuranosyl)pyrrolo[2,3d]pyrimidine (3.7)

Compound (3.6) 1.18 g, 2.0 mmol) and 4-methylmorpholine-N-oxide (0.704 g, 6.0 mmol) were mixed with 1,4-dioxane (20 ml) and the mixture set stirring. To the solution was added a solution of potassium osmate dihydrate (30 mg) in water (4 ml); the mixture was left to stir at room temperature for 24 hrs. The solvent was then evaporated under reduced pressure; the residue was partitioned between ethyl acetate and water. The organic layer was retained and washed twice with water, then with brine, then dried (MgSO$_4$), filtered and evaporated under reduced pressure. The residue was purified by flash column chromatography (silica. 4–7% methanol in chloroform) to give 160 mg (13%) of (3.7). $\delta_H$ (300 MHz, CDCl$_3$) 1.96+2.03 (1H total, 2×t, D$_2$O exch., 1°-OH), 2.30 (1H total, 2×d, D$_2$O exch., 2°-OH), 2.42+2.45 (each 3H, s, toluoyl —CH$_3$), 2.62 (3H, s, —SCH$_3$), 2.69–3.01 (4H, m, 2'-H$_{a,b}$+CH$_2$—CH(OH)—CH$_2$(OH)), 3.50+3.70 (each 1H, m, —CH$_2$(OH)), 3.95 (1H, m, —CH(OH)—), 4.57–4.78 (3H, m, 5'-H$_2$+4'-H, 5.75 (1H, m, 3'-H), 6.74 (1H, m, 1'-H), 7.11 (1H, s, 6-H), 7.21–7.31+7.88–8.00 (each 4H, m, toluoyl aryl-H) ppm.

2-(Methylthio)-4-chloro-5-(3-azido-2-hydroxypropyl)-7-(2-deoxy-3,5di-O-p-toluoyl-β-D-ribofuranosyl)pyrrolo[2,3d]pyrimidine (3.8)

Compound (3.7) (125 mg, 0.20 mmol) was dissolved in anhydrous N,N-dimethylformamide (3 ml). The solution was cooled to 0° C. in an ice-water bath, with stirring. To this was added triphenylphosphine (63 mg, 0.24 mmol), then carbon tetrabromide (80 mg, 0.24 mmol) and finally sodium azide (39 mg, 0.60 mmol). This mixture was stirred in the cooling bath for a further 1 hr, then stirred at room temperature for 16 hrs. The mixture was then partitioned between chloroform and dilute aqueous sodium bicarbonate solution. The organic layer was collected, washed with water and dried (MgSO$_4$), filtered and evaporated under reduced pressure to give a yellow gum. Purified by flash column chromatography (silica. 2.5% methanol in chloroform) and then prep. t.l.c. (silica. 6% methanol in chloroform) to give 40 mg of (3.8). δH (300 MHz, CDCl$_3$) 2.18 (1H , d, D$_2$O exch., 2°-OH), 2.43+2.45 (each 3H, s, toluoyl —CH$_3$), 2.62 (3H, s, —SCH$_3$), 2.69–3.01 (4H, m, 2'-H$_{a,b}$+CH$_2$—CH(OH)—CH$_2$(N$_3$)), {3.27 (1H, dd, J 12.5+6.6 Hz) and 3.37 (1H, dd, J 12.5+3.3 Hz), N$_3$—CH$_{a,b}$}, 4.00 (1H, m, —CH(OH)—), 4.57–4.79 (3H, m, 5'-H$_2$+4'-H), 5.74 (1H, m, 3'-H), 6.74 (1H, m, 1'-H), 7.12 (1H, s, 6-H), 7.25–7.31+7.88–8.00 (each 4H, m, toluoyl aryl-H) ppm.

EXAMPLE 4

The synthesis of the nucleoside analogue 1-(2-deoxyribofuranosyl)-pyrazolo[3,4-d]pyrimidine[2,3-c] dihydro-oxazepine (4.10) is described. Manipulations to introduce a reactive group as described in example 3 can also be applied to compound (4.5) in this example.

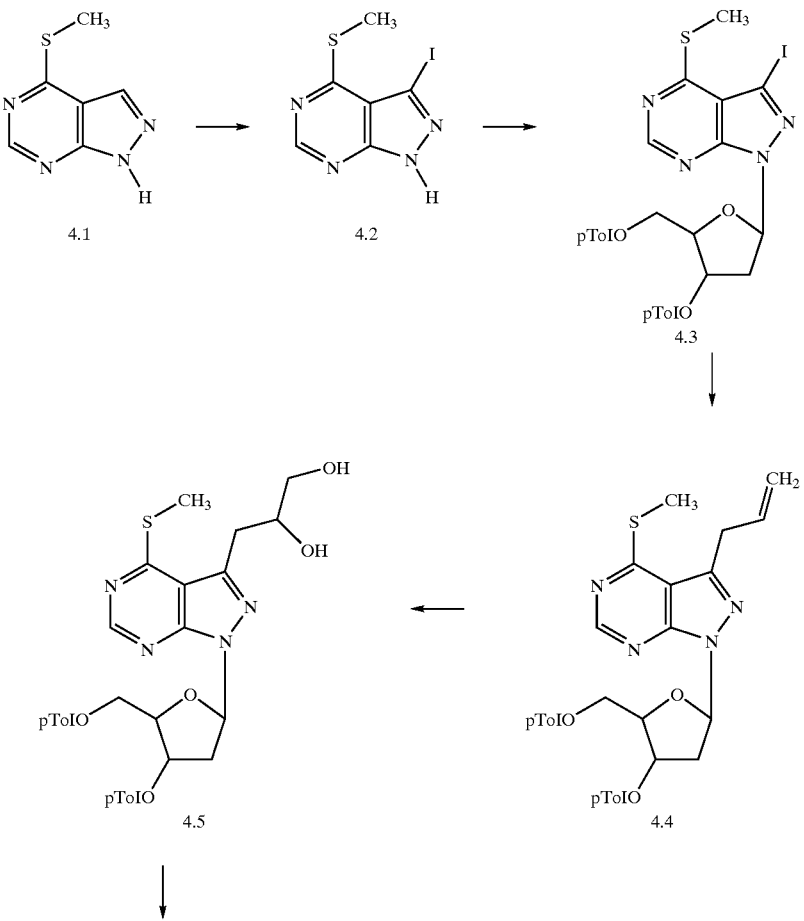

-continued
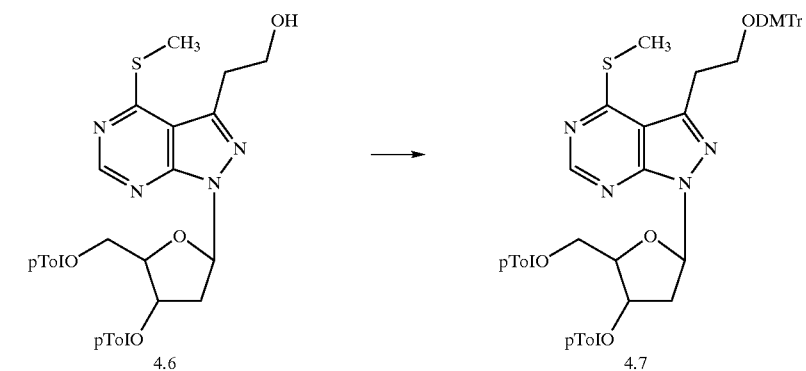
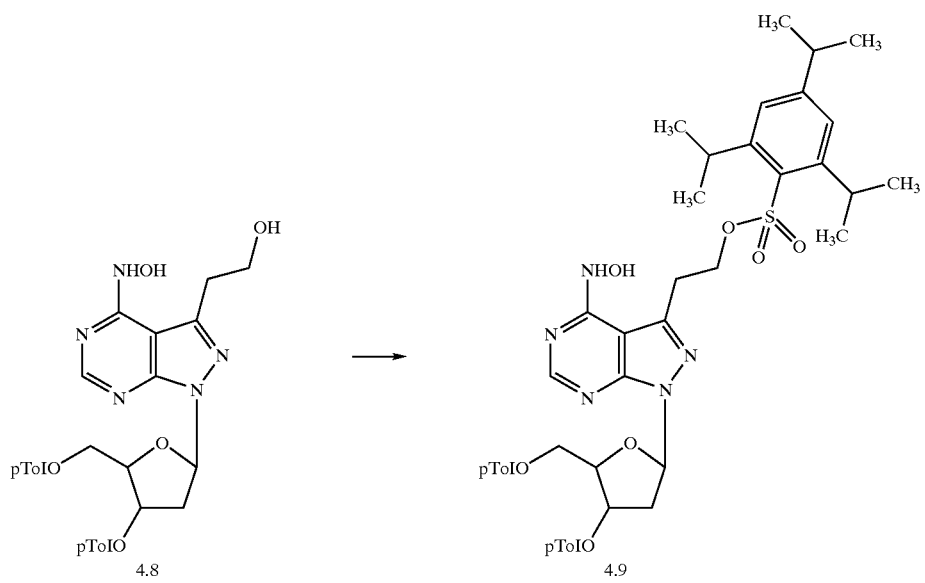
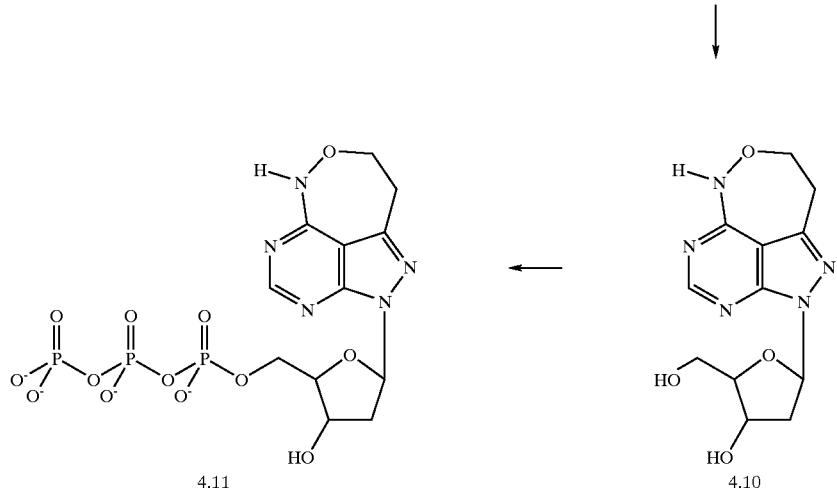

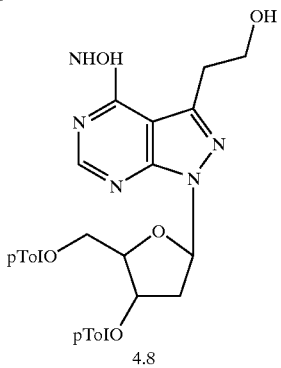

4.8

General

As for example 3.

4-methylmercapto-1H-pyrazolo-[3,4-d]pyrimidine (4.1)

4-Mercapto-1H-pyrazolo-[3,4-d]pyrimidine (7.0 g, 46.0 mmol) was suspended in NaOH solution (0.8M, 73 ml)) then iodomethane (7.2 g, 1.1 eq.) added. After 30 min. the solid formed was collected by filtration then recrystallised from water (250 ml). The product was dried under vacuum to yield a white solid (6.4 g, 84%). $R_f$ 0.65 (EtOAc/MeOH 9:1 v/v). $\delta_H$ (300 MHz, d6-DMSO); 2.69 (s, 3H, SCH$_3$), 8.29 (s, 1H, H3), 8.73 (s, 1H, H6) ppm. ESI-MS; [(M+H)$^+$] theoretical [(C$_6$H$_7$N$_4$S) 167.07] found 167.07.

3-Iodo-4-methylmercapto-1H-pyrazolo-[3,4-d]pyrimidine (4.2)

4-methylmercapto-1H-pyrazolo-[3,4-d]pyrimidine (4.1) (1.9 g, 11.8 mmol) was suspended in dichloroethane (60 ml) then N-iodosuccinimide (4.7 g, 2.0 eq.) added. The reaction mixture was refluxed for 2 h., the solid formed collected by filtration and recrystallised from EtOAc (200 ml) to yield the product as a white solid (3.0 g, 88%). $R_f$ 0.60 (EtOAc). $\delta_H$ (300 MHz, d6-DMSO); 2.64 (s, 3H, SCH$_3$), 8.69 (s, 1H, H6) ppm. ESI MS, [(M–H)$^-$] theoretical [(C$_6$H$_4$N$_4$IS) 291.04] found 290.98.

3-Iodo-4-methylmercapto-1-(2'-deoxy-3',5'-di-O-(p-toluoyl)-B-D-ribofuranosyl)-pyrazolo-[3,4-d]pyrimidine (4.3)

3-Iodo-4-methylmercapto-1H-pyrazolo-[3,4-d]pyrimidime (4.2) (2.1 g, 7.2 mmol) was dissolved in DMF (30 ml) then KOH (2.0 g, 5 eq.) and TDA-1 (0.5 ml) added. The reaction mixture was stirred for 15 min. then 2-deoxy-3,5-di-O-p-toluoyl-α-D-ribosyl chloride (3.2 g, 1.3 eq.) added. Stirring was continued for a further 15 min. then DCM (200 ml) added. The organic phase was washed with brine (sat., 3×100 ml), dried (MgSO$_4$), filtered, then evaporated to dryness in vacuo. The product was isolated as a white foam (1.6 g, 35%) by SiO$_2$ chromatography, eluting with Et$_2$O:pet ether 40–60 (3:7 v/v). $R_f$ 0.60 (Et$_2$O/pet. ether 40–60 1:1 v/v). $\delta_H$ (300 MHz, d6-DMSO); 2.37 (s, 3H, CH$_3$), 2.39 (s, 3H, CH$_3$), 2.66 (s, 3H, SCH$_3$), 2.73 (m, 1H, H2'), 3.22 (m, 1H, H2'), 4.46 (m, 3H, H4'& H5'), 5.76 (m, 1H, H3'), 6.80 (t, 1H, J 6.8 Hz, H1'), 7.34 (m, 4H, Ar—H), 7.84 (m, 4H, Ar—H), 8.78 (s, 1H, H6) ppm.

3-allyl-4-methylmercapto-1-(2'-deoxy-3',5'-di-O-(p-toluoyl)-B-D-ribofuranosyl)-pyrazolo-[3,4-d]pyrimidine (4.4)

3-Iodo-4-methylmercapto-1-(2'-deoxy-3',5'-di-O-(p-toluoyl)-B-D-ribofuranosyl)-pyrazolo-[3,4-d]pyrimidine (4.3) (1.0 g, 1.55 mmol) was dissolved in toluene (15 ml) then bis(triphenylphosphine)palladium (II) dichloride (32 mg, 3 mol %) and allyltributyltin (0.96 ml, 2 eq.) added. The reaction mixture was refluxed for 3 h. then stirred at room temperature for a further 16 h. To the reaction was added DCM (100 ml) then the organic phase washed with brine (3×100 ml), dried (MgSO$_4$), filtered, then evaporated to dryness in vacuo. The product was isolated as a colourless oil (0.40 g, 46%) by SiO$_2$ chromatography eluting with Et$_2$O:pet ether 40–60 (3:7 v/v). $R_f$ 0.60 (Et$_2$O/pet. ether 40–60 1:1 v/v). $\delta_H$ (300 MHz, CDCl$_3$); 2.40 (s, 3H, CH$_3$), 2.42 (s, 3H, CH$_3$), 2.63 (m, 1H, H2'), 2.70 (s, 3H, SCH$_3$), 3.52 (m, 1H, H2'), 3.77 (d, 2H, J 6.3 Hz, CH$_2$—CH=CH$_2$), 4.55 (m, 3H, H4'& H5'), 5.11 (m, 2H, CH$_2$—CH=CH$_2$), 5.87 (m, 1H, H3'), 6.03 (m, 1H, CH$_2$—CH=CH$_2$), 6.92 (t, 1H, J 6.6 Hz, H1'), 7.23 (m, 4H, Ar—H), 7.98 (m, 4H, Ar—H), 8.69 (s, 1H, H6) ppm.

3-(1,2-dihydroxypropane)-4-methylmercapto-1-(2'-deoxy-3',5'-di-O-(p-toluoyl)-B-D-ribofuranosyl)-pyrazolo-[3,4-d]pyrimidine (4.5)

3-Allyl-4-methylmercapto-1-(2'-deoxy-3',5'-di-O-(p-toluoyl)-B-D-ribofuranosyl)-pyrazolo-[3,4-d]pyrimidine (4.4) (400 mg, 0.72 mmol) was dissolved in acetone (5 ml) then N-methylmorpholine-N-oxide (250 mg, 3 eq.) added. Water (2 ml) was added followed by potassium osmate hydrate (10 mg) and the reaction mixture stirred at room temperature for 3 h. The solvent was removed in vacuo then the product isolated as a white foam (350 mg, 85%) by SiO$_2$ chromatography eluting with EtOAc. $R_f$ 0.30 (EtOAc). $\delta_H$ (300 MHz, CDCl$_3$); 2.40 (s, 3H, CH$_3$), 2.44 (s, 3H, CH$_3$), 2.66 (m, 1H, H2'), 2.71 (s, 3H, SCH$_3$), 3.21 (m, 2H, CH$_2$CHOH), 3.51 (m, 1H, H2'), 3.62 (m, 2H, CH$_2$OH), 4.31 (m, 1H, CHOH), 4.60 (m, 3H, H4'& H5'), 5.89 (m, 1H, H3'), 6.93 (m, 1H, H1'), 7.22 (m, 4H, Ar—H), 7.94 (m, 4H, Ar—H), 8.69 (s, 1H, H6) ppm.

3-(1-hydroxyethane)-4-methylmercapto-1-(2'-deoxy-3',5'-di-O-(p-toluoyl)-B-D-ribofuranosyl)-pyrazolo-[3,4-d]pyrimidine (4.6)

3-(1,2-Dihydroxypropane)-4-methylmercapto-1-(2'-deoxy-3',5'-di-O-(p-toluoyl)-B-D-ribofuranosyl)-pyrazolo-[3,4-d]pyrimidine (4.5) (360 mg, 0.61 mmol) was dissolved in dioxane/H$_2$O (4:1 v/v, 5 ml) then NaIO$_4$ (170 mg, 1.6 eq.) in H$_2$O (1 ml) added. The reaction mixture was stirred at room temperature for 3 h. then filtered through Celite. The filtrate was evaporated to dryness in vacuo then redissolved in THF (5 ml) to which was added NaBH$_4$ (30 mg, 1.1 eq.). The reaction mixture was stirred at room temperature for a further 30 min. then evaporated to dryness in vacuo. The residue was dissolved in DCM (50 ml) then the organic phase washed with water (3×50 ml), brine (sat., 50 ml), dried (MgSO$_4$), filtered, then evaporated to dryness in vacuo. The product was isolated as a white foam (230 mg, 67%) by SiO$_2$ chromatography eluting with EtOAc/pet ether 40–60 (1:1 v/v). R$_f$ 0.55 (EtOAc). δ$_H$ (300 MHz, CDCl$_3$); 2.40 (s, 3H, CH$_3$), 2.44 (s, 3H, CH$_3$), 2.64 (m, 1H, H2'), 2.71 (s, 3H, SCH$_3$), 3.27 (t, 2H, J 5.6 Hz, CH$_2$CH$_2$OH), 3.53 (m, 1H, CH$_2$CH$_2$OH), 4.61 (m, 3H, H4' & H5'), 5.87 (m, 1H, H3'), 6.92 (t, 1H, J 6.6 Hz, H1'), 7.23 (m, 4H, Ar—H), 7.95 (m, 4H, Ar—H), 8.69 (s, 1H, H6) ppm.

3-(1-O-(4,4'-dimethoxytrityl)hydroxyethane)-4-methylmercapto-1-(2'-deoxy-3',5'-di-O-(p-toluoyl)-B-D-ribofuranosyl)-pyrazolo-[3,4-d]pyrimidine (4.7)

3-(1-Hydroxyethane)-4-methylmercapto-1-(2'-deoxy-3',5'-di-O-(p-toluoyl)-B-D-ribofuranosyl)-pyrazolo-[3,4-d]pyrimidine (4.6) (420 mg, 0.75 mmol) and DMAP (20 mg) were dissolved in pyridine (5 ml) then 4,4'-dimethoxytrityl chloride (330 mg, 1.3 eq.) added. The reaction mixture was stirred at room temperature for 3 h. then DCM (50 ml) added. The organic phase was washed with NaHCO$_3$ (sat., 50 ml), brine (sat., 50 ml), dried (MgSO$_4$), filtered, then evaporated to dryness in vacuo. The product was isolated as a white foam (640 mg, 94%) by SiO$_2$ chromatography eluting with Et$_2$O. R$_f$ 0.75 (Et$_2$O). δ$_H$ (300 MHz, CDCl$_3$); 2.36 (s, 3H, CH$_3$), 2.43 (s, 3H, CH$_3$), 2.60 (m, 2H, H2'), 2.71 (s, 3H, SCH$_3$), 3.31 (t, 2H, J 5.8 Hz, CH$_2$CH$_2$OH), 3.50 (t, 2H, J 5.8 Hz, CH$_2$CH$_2$ODMTr), 4.52 (m, 3H, H4' & H5'), 5.84 (m, 1H, H3'), 6.71 (m, 4H, Ar—H), 6.90 (t, 1H, J 6.7 Hz, H1'), 7.16–7.36 (m, 13H, Ar—H), 7.98 (t, 4H, J 9.0 Hz, Ar—H), 8.66 (s, 1H, H6) ppm.

3-(1-hydroxyethane)-4-N-hydroxyamino-1-(2'-deoxy-3',5'-di-O-(p-toluoyl)-B-D-ribofuranosyl)-pyrazolo-[3,4-d]pyrimidine (4.8)

3-(1-O-(4,4'-dimethoxytrityl)hydroxyethane)4-methylmercapto-1-(2'-deoxy-3',5'-di-O-(ptoluoyl)-B-D-ribofuranosyl)-pyrazolo-[3,4-d]pyrimidine (4.7) (640 mg, 0.75 mmol) was dissolved in pyridine (6 ml) then hydroxylamine hydrochloride (520 mg, 10 eq.) added. The solution was refluxed for 1 h. then stirred at room temperature for 16 h. The solvent was removed in vacuo then the product isolated as a pale purple foam (290 mg, 71%) by SiO$_2$ chromatography eluting with CHCl$_3$/MeOH (0–10% v/v). R$_f$ 0.10 (EtOAc). δ$_H$ (300 MHz, CDCl$_3$); 2.37 (s, 3H, CH$_3$), 2.41 (s, 3H, CH$_3$), 2.60 (m, 1H, H2'), 3.02 (m, 2H, CH$_2$CH$_2$OH), 3.40 (m, 1H, H2'), 3.78 (m, 1H, CH$_2$CH$_2$OH), 4.56 (m, 3H, H4' & H5'), 5.82 (m, 1H, H3'), 6.65 (t, 1H, J 6.5 Hz, H1'), 7.23 (m, 4H, Ar—H), 7.93 (m, 4H, Ar—H), 8.59 (s, 1H, H6) ppm. ESI-MS; [(M–H)$^-$] theoretical [(C$_{28}$H$_{28}$N$_5$O$_7$) 546.20] found 546.13.

3-(1-O-(triisopropylbenzenesulfonyl)-hydroxyethane)-4-N-hydroxyamino-1-(2'-deoxy-3',5'-di-O-(p-toluoyl)-B-D-ribofuranosyl)-pyrazolo-[3,4-d]pyrimidine (4.9)

3-(1-Hydroxyethane)-4-N-hydroxyamino-1-(2'-deoxy-3',5'-di-O-(p-toluoyl)-B-D-ribofuranosyl)-pyrazolo-[3,4-d]pyrimidine (4.8) (290 mg, 0.53 mmol) was dissolved in pyridine (5 ml) then triisopropylbenzenesulfonyl (177 mg, 1.1 eq.) added. The reaction mixture was stirred at room temperature for 16 h. then DCM (50 ml) added. The organic phase was washed with brine (sat., 50 ml), dried (MgSO$_4$), filtered, then evaporated to dryness in vacuo. The product was isolated as a white foam (310 mg, 72%) by SiO$_2$ chromatography eluting with Et$_2$O. Rf 0.80 (EtOAc). δ$_H$ (300 MHz, CDCl$_3$); 1.24 (d, 18H, J 6.0 Hz, (CH$_3$)$_2$CH), 2.36 (s, 3H, CH$_3$), 2.40 (s, 3H, CH$_3$), 2.59 (m, 1H, H2'), 2.78 (t, 2H, J 5.8 Hz, CH$_2$CH$_2$OS), 3.40 (m, 1H, H2'), 3.62 (m, 1H, CH$_2$CH$_2$OH), 4.12 (septet, 1H, J 6.0 Hz, CH(CH$_3$)$_2$),4.53 (m, 3H, H4' & H5'), 5.78 (m, 1H, H3'), 6.62 (t, 1H, J 6.6 Hz, H1'), 7.23 (m, 6H, Ar—H), 7.62 (s, 1H, H6), 7.92 (m, 4H, Ar—H) ppm. ESI-MS; [(M–H)$^-$] theoretical [(C$_{43}$H$_{50}$N$_5$O$_9$S) 812.36] found 812.10.

1-(2'-deoxyribofuranosyl)-pyrazolo[3,4-d]pyrimidine [2,3-c]dihydro-oxazepine (4.10)

3-(1-O-(triisopropylbenzenesulfonyl)-hydroxyethane)4-N-hydroxyamino-1-(2'-deoxy-3',5'-di-O-(p-toluoyl)-B-D-ribofuranosyl)-pyrazolo-[3,4-d]pyrimidine (4.9) (310 mg, 0.38 mmol) was dissolved in t-butanol (5 ml) then potassium t-butoxide (257 mg, 6 eq.) added. The reaction mixture was stirred at room temperature for 1 h. then AcOH added to pH 7. The solvent was removed in vacuo then the product isolated as a brown oil (17 mg, 15%) by SiO$_2$ chromatography eluting with CHCl$_3$/MeOH (0–30% v/v). The crude product containing fractions were subsequently purified by reverse phase HPLC eluting with MeOH/H$_2$O (10–100% v/v) over 60 min. at a flow rate of 3 ml/min. R$_f$ 0.05 (CHCl$_3$/MeOH 30% v/v). δ$_H$ (300 MHz, CD$_3$OD); 2.30 (m, 1H, H2'), 2.93 (m, 1H, H2'), 3.15 (m, 2H, CH$_2$CH$_2$O), 3.50–4.02 (m, 5H, H4'+H5'+OCH$_2$CH$_2$), 4.60 (m, 1H, H3'), 6.59 (m, 1H, H1'), 8.11 (s, 1H, H6) ppm. ESI-MS; [(M–H)$^-$] theoretical [(C$_{12}$H$_{14}$N$_5$O$_4$) 292.10] found 292.11.

1-(2'-deoxy-5'-O-triphosphate-ribofuranosyl)-pyrazolo[3,4-d]pyrimidine [2,3-c]dihydro-oxazepine (4.11)

1-(2'-deoxyribofuranosyl)-pyrazolo[3,4-d]pyrimidine[2,3-c]dihydro-oxazepine (4.10) (17 mg, 58 μmol) was dissolved in triethylphosphate/trimethylphosphate (1:1 v/v, 1 ml) then stirred at 0° C. for 1 h. To the solution was added POCl$_3$ (18.4 μl, 0.2 mmol) at 0° C. and the reaction mixture stirred for a further 2 h. Tributylammonium pyrophosphate in DMF (0.5M, 3 ml) and tri-n-butylamine (0.4 ml) were added and the reaction mixture stirred at room temperature for 1 h. Triethylammonium bicarbonate (1M, pH8.5, 20 ml) was added and the reaction mixture stored at 4° C. for 16 h. then evaporated to dryness in vacuo. The residue was dissolved in water (15 ml) then the product purified by ion exchange chromatography (8 μM Hipex anion exchange column) eluting with 0–100% triethylammonium bicarbonate (0.3M) over 100 min at a flow rate of 4 ml/min. The collected fractions were subsequently purified by reverse phase chromatography using a Waters C18 Sep Pak cartridge (35 cc). δ$_P$ (300 MHz, D$_2$O); –7.95 (m), –10.80 (m), –22.03 (m) ppm.

EXAMPLE 5 a) The incorporation of dSTP into DNA by DNA polymerases was examined in primer extension assays. A series of 10 µl reactions was performed for each of three DNA polymerases: Taq polymerase (Promega), the Klenow fragment of E. coli DNA polymerase I (Boehringer Mannheim) and the 3' to 5' exonuclease-free version of Klenow fragment (New England Biolabs). Each reaction contained 1 pmol of a 24-mer oligonucleotide: 5' GATCTGGTCATAGCT-GTTTCCTGT (SEQ ID NO. 1) annealed to 0.25 pmol of a complementary 20-mer oligonucleotide 5' ACAGGAAA-CAGCTATGACCA (SEQ ID NO. 2) which was labelled at the 5' end with 32P, and 1 µl of 10×buffer (for Taq polymerase: 500 mM KCl, 100 mM Tris pH 9 at room temperature, 1% Triton-X 100, 15 mM MgCl2; for the other two enzymes: 50 mM MgCl2, 100 mM Tris pH 7.5 at room temperature, 75 mM DTT). Normal dNTPs, in various combinations, were added, as required, to 50 µM final concentration; dSTP was also used at 50 µM final concentration.

For each enzyme four reactions were performed:
i) no added dNTPs;
ii) plus dSTP;
iii) plus dSTP and TTP;
iv) plus dSTP, TTP and dCTP.
[See Nucleic Acids Res (1998), 26, 1144–1149; for the equivalent experiment with dKTP and Taq polymerase].

A single unit of the appropriate polymerase was added to start each of the reactions; these were incubated for 15 minutes (at 72° C. under mineral oil for Taq, at 37° C. for Pol I derivatives) before being terminated by the addition of 5 µl of termination mix (95% formamide, 20 mM EDTA, 0.05% Bromophenol Blue, 0.05% Xylene Cyanol FF). The reactions were heated to 70° C. for ten minutes before electrophoresis on a 20% polyacrylamide/7M urea gel, which was then exposed to autoradiography film.

The results can be summarised as follows: All three polymerases can incorporate dSTP as either dGTP or as dATP, that is opposite T or C in a template, but not opposite A or G, because no extension occurs in any of the assays opposite A or G unless TTP or dCTP are present.

b) A second primer extension assay was used to compare the triphosphate of the pyrrolo compound (1.14) (dSTP) with the triphosphate of the pyrazolo compound (4.11) as substrates for the 3' to 5' exonuclease-free version of Klenow fragment of DNA polymerase I (EFK). The assay used a $^{33}$P 5' end labelled 15 mer primer hybridised to one of two different 24 mer templates. The sequences of the primer and templates are:

Primer 5' TGCATGTGCTGGAGA 3' (SEQ ID NO. 3)
Template 1 3' ACGTACACGACCT CTCTTGATCAG 5' (SEQ ID NO. 4)
Template 2 3' ACGTACACGACCTCT ACCTTGCTA 5' (SEQ ID NO.5)

One picomole $^{33}$P labelled primer was hybridised to 2 picomoles of template in ×2 Klenow buffer. To this was added either 4 µM dNTPαS, 20 µM or 80 µM analogue triphosphate or a mixture of 4 µM dNTPαS and 20 or 80 µM analogue triphosphate. Two units EFK and 2 mU inorganic pyrophosphatase were used per reaction. Primer alone, primer plus template, primer plus template plus enzyme controls were also carried out. The reactions were incubated at 37° C. for 3 minutes. Reactions were then stopped by the addition of formamide EDTA stop solution. Reaction products were separated on a 19% polyacrylamide 7M urea gel and the product fragments sized by comparison with a $^{33}$P labelled 8 to 32 base oligonucleotide ladder after exposure to Kodak Biomax autoradiography film.

Using the first template and dSTP alone the +3 product (i.e. primer extended by 3 nucleotides) was observed showing that dSTP was efficiently incorporated in place of both G and A. The dGTPαS plus dATPαS control +3 extension product band ran in a similar position to that of the dSTP alone +3 product band. Compound (4.11) however did not extend with this template when it was the only nucleotide present, but did produce a +3 product in the presence of dGTP, indicating that at these concentrations it was behaving as A. Further extension following the incorporation of two compound (4.11) residues did not occur.

Using the second template and a mixture of dTTPαS and dSTP the +2, +3 and +5 products were observed but no +1 product. This shows that the dSTP is efficiently incorporated as a single G but that multiple additions as G are slow. The +5 product band comes from the efficient multiple incorporation of dSTP as A. This appears to indicate that the tautomeric ratio favours that of the A rather than the G derivative. Results with this template also confirmed that compound (4.11) behaved as A rather than G and the incorporation of two (4.11) residues resulted in termination.

EXAMPLE 6

In order to test the ability of the triphosphate of the pyrrolo compound (1.14) (dSTP) and the triphosphate of the pyrazolo compound (4.11) to be accepted by terminal deoxynucleotidyl transferase as a substrate, an oligonucleotide tailing reaction was performed.

A 15 mer primer (sequence: 5' TGC ATG TGC TGG AGA 3') (SEQ ID NO. 6) and 8 to 32 base oligonucleotide markers were 5' end labelled with [y$^{33}$P] ATP and T4 polynucleotide kinase. Reactions were boiled for 5 minutes after labelling to remove any PNK activity. Four picomoles of the labelled primer, 25 U terminal deoxynucleotidyl transferase and 64 µM dNTP or analogue triphosphate were incubated in 25 µl 100 mM cacodylate buffer pH7.2, 2 mM CoCl$_2$ and 0.2 mM 2-mercaptoethanol for 90 minutes at 37° C. The reactions were stopped by the addition of formamide stop solution and the reaction products run on a 19% polyacrylamide 7M urea gel with the labelled markers. Autoradiography using Biomax film was carried out on the dry gel.

The results showed that dATP gave a tail estimated at greater than 100 bases long and dGTP produced shorter tails in the order of 50 bases. The pyrrolo analogue (dSTP) produced tails intermediate in size between those of dATP and dGTP. The pyrazolo analogue extended the primer predominantly by a single base although there were some +2 and +3 products as well as some unextended primer.

EXAMPLE 7

The incorporation of dSTP and the pyrazolo compound (4.11) into DNA by ThermoSequenase™ DNA polymerase was examined in cycle sequencing reactions.

The following nucleotide mixes were made up:
a) Standard dNTP mix 7.5 µM dATP, dCTP, dGTP, dTTP b) Standard dITP mix 7.5 $\mu$M dATP, dCTP, dTTP and 37.5 $\mu$M dITP c) 8-oxo-dGTP mix 7.5 $\mu$M dATP, dCTP, dTTP and 160 $\mu$M 8-oxo-dGTP d) dSTP "A" mix 7.5 $\mu$M dCTP, dGTP, dTTP and 40 $\mu$M dSTP e) Compound (4.11) "A" mix 7.5 $\mu$M dCTP, dGTP, dTTP and 40 $\mu$M compound (4.11)

f) dSTP "G" mix 7.5 $\mu$M dATP, dCTP, dTTP and 80 $\mu$M dSTP g) Compound (4.11) "G" mix 7.5 $\mu$M dATP, dCTP, dTTP and 80 $\mu$M compound (4.11)

The following reaction master mix was made up:
16 $\mu$l Reaction buffer
80 $\mu$l DNA (M13 mp 18 0.2 $\mu$g/$\mu$l
18 $\mu$l Primer (-40 forward sequencing 24 mer 2 pmole/$\mu$l)
16 $\mu$l ThermoSequenase™ (4U/$\mu$l)
30 $\mu$l Water
160 $\mu$l Total volume All reagents were from ThermoSequenase radiolabelled terminator cycle sequencing kit (US79750 Amersham life Science). [$\alpha^{33}$P] ddNTP's were from Amersham Pharmacia Biotech (code AH9539).

Reactions 1
2 $\mu$l nucleotide mix a)
0.5 $\mu$l [$\alpha^{33}$P] ddATP
4.5 $\mu$l reaction master mix Reaction 2
2 $\mu$l nucleotide mix a)
0.5 $\mu$l [$\alpha^{33}$P] ddCTP
4.5 $\mu$l reaction master mix Reaction 3
2 $\mu$l nucleotide mix a)
0.5 $\mu$l [$\alpha^{33}$P] ddGTP
4.5 $\mu$l reaction master mix Reaction 4
2 $\mu$l nucleotide mix a)
0.5 $\mu$l [$\alpha^{33}$P] ddTTP
4.5 $\mu$l reaction master mix Reactions 5–8
as above except 2 $\mu$l nucleotide mix b) was used.

Reactions 9–12
as above except 2 $\mu$l nucleotide mix c) was used.

Reactions 13–16
as above except 2 $\mu$l nucleotide mix d) was used.

Reactions 17–20
as above except 2 $\mu$l nucleotide mix e) was used.

Reactions 21–24
as above except 2 $\mu$l nucleotide mix f) was used.

Reactions 25–28
as above except 2 $\mu$l nucleotide mix g) was used.

All reactions were overlayed with mineral oil and then cycled as follows:
95° C. 30 seconds
55° C. 30 seconds
72° C. 120 seconds
for 10 cycles.

The reactions were then heated at 95° C. for 2 minutes before loading onto a 6% polyacrylamide 7M urea gel. The gel was run at 48 mA for 90 minutes. After fixing in 10% acetic acid/10% methanol the gel was dried and exposed to Kodak Biomax autoradiography film.

The results can be summarised as follows:

The dSTP "A" mix gave a sequence (>250 bases) with similar even band intensities. The sequence was longer than that obtained with both dITP (<200 bases) and 8-oxo-dGTP. In fact the 8-oxo dGTP sequence only extended 15–20 bases from the primer. The dITP sequence had uneven band intensities especially in the G track.

No sequence data was obtained using the other 3 nucleotide mixes.

This shows that, unlike dITP, dSTP is a very good polymerase substrate and that a G equivalent could be useful in removing compression artefacts from sequencing reactions by replacing the 7-deaza-dGTP or dITP analogues currently used.

What is claimed is:

1. A compound having the structure (2)

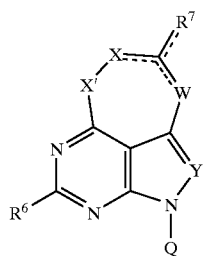

(2)

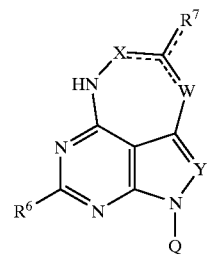

(3)

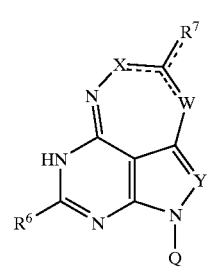

(4)

wherein

W is an alkylenyl or an alkenylenyl chain with 0–2 carbon atoms any of which may carry a substituent $R^8$, X is selected from the group consisting of O, N, $NR^{12}$ and $CR^{10}$, X' is selected from the group consisting of O, S, NH, and N, and when X' is N, tautomers of structures (3) and (4) are present, when
X' is O or S, X is C, Y is CH or N, R⁶ is selected from the group consisting of H, NH₂, SCH₃, SO₂CH₃ and NHNH₂, R⁷ and R⁸ are independently selected from the group consisting of H, F, alkyl, alkenyl, aryl, acyl and a reporter moiety, R⁹ and R¹² are independently selected from the group consisting of H, alkyl, alkenyl, aryl, acyl, and a reporter moiety, R¹⁰ is selected from the group consisting of H, =O, F, alkyl, alkenyl, aryl, acyl and a reporter moiety, the dashed line in structure (2) indicates an optional double bond, Q is selected from the group consisting of H,

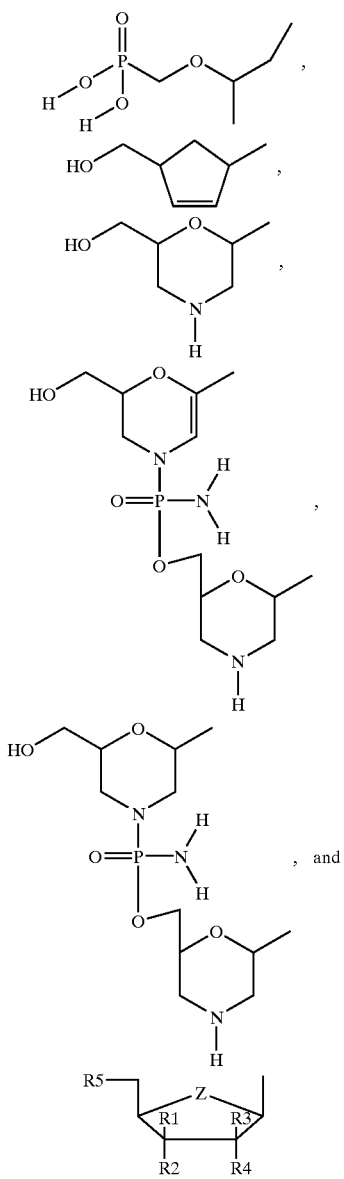

wherein

R is selected from the group consisting of CH₃, CH₂OH and H,

Z is selected from the group consisting of O, S, SO, and CH₂,

R¹, R³ and R⁴ are independently selected from the group consisting of H, OH, F, NH₂, N₃, O-hydrocarbyl, and a reporter moiety, R² is selected from the group consisting of H, OH, F, NH₂, N₃, O-hydrocarbyl, a report moiety, phosphoramidite, H-phosphonate, methylphosphonate and phosphorothioate, R⁵ is selected from the group consisting of OH, SH, NH₂, monophosphate, diphosphate, triphosphate, thiophosphate, boranophosphate, phosphoramidite, H-phosphonate, methylphosphonate, and phosphorothioate, and at least one of R² and R⁵ being selected from the group consisting of phosphoramidite, H-phosphonate, methylphosphonate, and phosphorothioate.

2. A compound according to claim 1, wherein at least one of R¹, R², R³, R⁴, R⁵, R⁷, R⁸, R⁹, R¹⁰ or R¹² is a reporter group.

3. A compound according to claim 1, wherein said reporter moiety consists of a signal moiety and a linker group.

4. A polynucleotide containing at least one residue of a nucleoside analogue according to claim 1.

5. A polynucleotide according to claim 4, wherein a signal moiety has been introduced into the incorporated nucleoside analogue residue.

6. 9-(2'-Deoxy-5'-O-triphosphoryl-ribofuranosyl)-pyrrolo[4,3,2-de]pyrimido[4,5-c]dihydro-oxazepine (dSTP).

7. 1-(2'-deoxy-5'-O-triphosphoryl-ribofuranosyl)-pyrazolo[3,4-d]pyrimido[2,3-c]dihydro-oxazepine.

8. A chain extension method which comprises reacting a polynucleotide with a nucleoside triphosphate analogue according to claim 1 in the presence of a polymerase or a terminal deoxynucleotidyl transferase enzyme.

9. A chain extension method as claimed in claim 8, wherein the nucleoside thriphophate analogue is labelled with a reporter group either before or after being incorporated in the polynucleotide.

10. A compound according to claim 1, wherein
W is CH₂
X is O
X' is N
Y is CH or N
R⁶ is H or NH₂ and
R⁷ is H or reporter moiety.

11. A method of detecting the polynucleotide according to claim 4 or claim 5, which method comprises using for detection an antibody which binds to the base of the nucleoside analogue residue.

12. An oligonucleotide comprising the compound of claim 1 wherein Q is a nucleic acid backbone consisting of sugar-phosphate repeats or modified sugar-phosphate repeats or a backbone analogue consisting of polyamide nucleic acid (PNA).

13. A compound according to claim 1 or claim 10, wherein R⁵ is triphosphate.

14. A compound according to claim 1 or claim 10, wherein one of R² and R⁵ is phosphoramidite or H-phosphonate.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide

<400> SEQUENCE: 1
gatgtggtca tagctgtttc ctgt                                          24

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
acaggaaaca gctatgacca                                               20
```

-continued

```
<210> SEQ ID NO 3
<211> LENGTH: 15
<212> TYPE: DNA
<213> ORGANISM: Artificial Sequence
<220> FEATURE:
<223> OTHER INFORMATION: Primer

<400> SEQUENCE: 3
tgcatgtgct ggaga                                                    15

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
acgtacacga cctctcttga tcag                                          24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide

<400> SEQUENCE: 5
acgtacacga cctctacctt gcta                                          24

<210> SEQ ID NO 6
<211> LENGTH: 15
<212> TYPE: DNA
<213> ORGANISM: Artificial Sequence
<220> FEATURE:
<223> OTHER INFORMATION: Primer

<400> SEQUENCE: 6
tgcatgtgct ggaga                                                    15
```